United States Patent
Kunz et al.

(10) Patent No.: US 7,999,137 B2
(45) Date of Patent: Aug. 16, 2011

(54) PESTICIDE BI-PHENYL-AMIDINE DERIVATIVES

(75) Inventors: Klaus Kunz, Düsseldorf (DE); Jörg Greul, Leichlingen (DE); Oliver Guth, Leverkusen (DE); Benoît Hartmann, Sainte Foy-lès-Lyon (FR); Kerstin Ilg, Köln (DE); Wahed Ahmed Moradi, Monheim an Rhein (DE); Thomas Seitz, Langenfeld (DE); Peter Dahmen, Neuss (DE); Arnd Voerste, Köln (DE); Ulrike Wachendorff-Neumann, Neuwied (DE); Mark Drewes, Langenfeld (DE); Ralf Dunkel, Lyons (FR); Ronald Ebbert, Nürnberg (DE); Herbert Gayer, Monheim Am Rhein (DE); Stefan Hillebrand, Neuss (DE); Eva-Maria Franken, Leichlingen (DE); Olga Malsam, Rösrath (DE); Ulrich Ebbinghaus-Kintscher, Dortmund (DE)

(73) Assignee: Bayer Cropscience AG, Monheim (DE)

( * ) Notice: Subject to any disclaimer, the term of this patent is extended or adjusted under 35 U.S.C. 154(b) by 508 days.

(21) Appl. No.: 12/063,659

(22) PCT Filed: Sep. 12, 2006

(86) PCT No.: PCT/EP2006/066271
§ 371 (c)(1),
(2), (4) Date: Jul. 14, 2008

(87) PCT Pub. No.: WO2007/031512
PCT Pub. Date: Mar. 22, 2007

(65) Prior Publication Data
US 2008/0280992 A1 Nov. 13, 2008

(51) Int. Cl.
*C07C 257/00* (2006.01)
*A01N 25/26* (2006.01)

(52) U.S. Cl. ........................... 564/245; 504/100

(58) Field of Classification Search .............. 564/245; 514/637; 504/100
See application file for complete search history.

(56) References Cited

U.S. PATENT DOCUMENTS

| | | | |
|---|---|---|---|
| 5,633,218 A | 5/1997 | Spedding et al. | |
| 2010/0093534 A1* | 4/2010 | Kunz et al. | 504/100 |
| 2010/0113276 A1* | 5/2010 | Kuhn et al. | 504/242 |

FOREIGN PATENT DOCUMENTS

| | | |
|---|---|---|
| WO | WO 00/46184 | 8/2000 |
| WO | WO 02/055510 | 7/2002 |

* cited by examiner

*Primary Examiner* — Janet L. Andres
*Assistant Examiner* — John Mabry
(74) *Attorney, Agent, or Firm* — Baker Donelson Bearman, Caldwell & Berkowitz, PC

(57) ABSTRACT

The present invention relates to bi-phenyl-amidine derivatives of formula (I) in which the substituents are as in the description, their process of preparation, their use as fungicide or insecticide active agents, particularly in the form of fungicide or insecticide compositions, and methods for the control of phytopathogenic fungi or damaging insects, notably of plants, using these compounds or compositions:

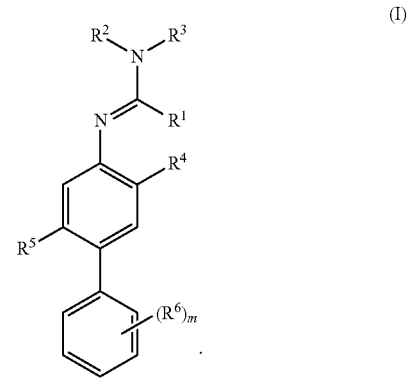

13 Claims, 1 Drawing Sheet

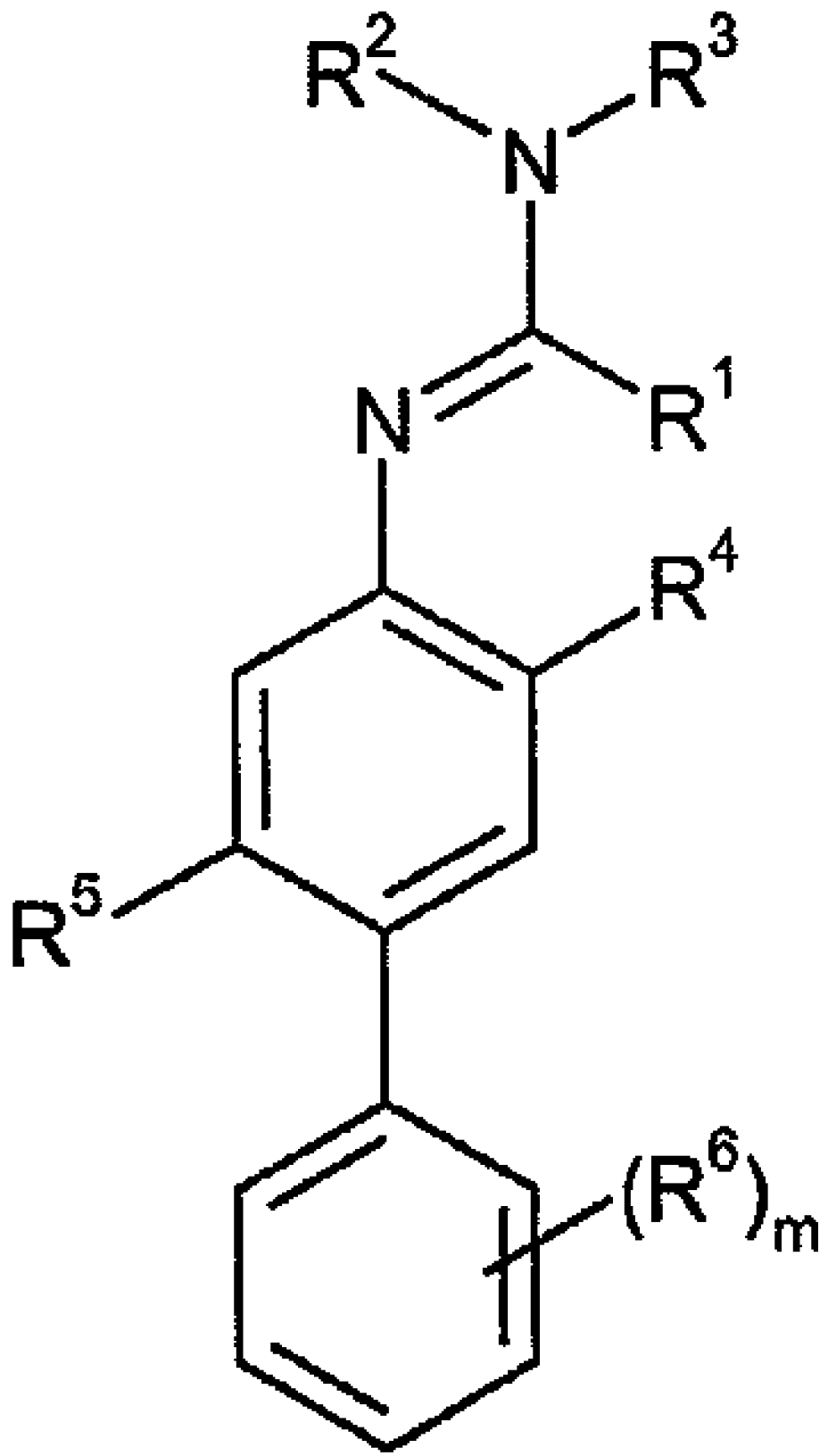

PESTICIDE BI-PHENYL-AMIDINE DERIVATIVES

CROSS REFERENCE TO RELATED APPLICATIONS

This is a §371 National Stage Application of International Application No. PCT/EP2006/066271 filed Sep. 12, 2006, which claims priority from European Application No. 05356153.6 filed Sep. 13, 2005.

BACKGROUND OF THE INVENTION

1. Field of the Invention

The present invention relates to bi-phenyl-amidine derivatives, their process of preparation, their process of preparation, their use as fungicide or insecticide active agents, particularly in the form of fungicide or insecticide compositions, and methods for the control of phytopathogenic fungi or damaging insects, notably of plants, using these compounds or compositions.

2. Description of Related Art

In international patent application WO-00/46184 certain phenyl-amidine derivatives are disclosed. However, this document does not specifically disclose nor suggest to select such compounds wherein the phenyl ring is substituted according to the invention thus allowing an unexpected and significantly higher fungicide activity.

It is always of high-interest in agriculture to use novel pesticide compounds in order to avoid or to control the development of resistant strains to the active ingredients. It is also of high-interest to use novel compounds being more active than those already known, with the aim of decreasing the amounts of active compound to be used, whilst at the same time maintaining an effectiveness at least equivalent to the already known compounds.

In the same way, it is also always of high-interest to use novel insecticide, namatocide or acaricide agents to control damaging insects or other damaging organisms.

SUMMARY OF THE INVENTION

We have now found a new family of compounds which possess the above mentioned effects or advantages.

Accordingly, the present invention provides bi-phenyl-amidine derivatives of formula (I):

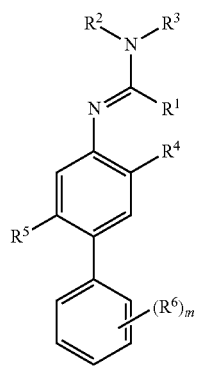

(I)

wherein $R^1$ represents H, a substituted or non substituted $C_1$-$C_{12}$-alkyl, a substituted or non substituted $C_2$-$C_{12}$-alkenyl, a substituted or non substituted $C_2$-$C_{12}$-alkynyl, SH or a substituted or non substituted S—$C_1$-$C_{12}$-alkyl;

$R^2$ represents a substituted or non substituted $C_1$-$C_{12}$-alkyl $R^3$ represents a substituted or non substituted $C_2$-$C_{12}$-alkyl, substituted or non substituted $C_3$-$C_6$-cycloalkyl, substituted or non substituted $C_2$-$C_{12}$-alkenyl, substituted or non substituted $C_2$-$C_{12}$-alkynyl, halogeno-$C_1$-$C_{12}$-alkyl; or $R^1$ and $R^2$, $R^1$ and $R^3$ or $R^2$ and $R^3$ can form together a substituted or non substituted 5 to 7-membered heterocycle;

$R^4$ represents a substituted or non substituted $C_1$-$C_{12}$-alkyl, a halogen atom, halogeno-$C_1$-$C_{12}$-alkyl, substituted or non substituted O—$C_1$-$C_{12}$-alkyl or cyano;

m represents 0, 1, 2, 3, 4 or 5;

$R^5$ represents H, a substituted or non substituted $C_1$-$C_{12}$-alkyl, a halogen atom, halogeno-$C_1$-$C_{12}$-alkyl, substituted or non substituted O—$C_1$-$C_{12}$-alkyl or cyano;

$R^6$, which may the same or different, represents H, a halogen atom, nitro, cyano trialkylsilyl, $C_1$-$C_8$-alkyl, substituted or non-substituted $C_1$-$C_4$-alkyl-phenyl, substituted or non-substituted phenyl, $C_1$-$C_4$-alkoxy, $C_1$-$C_4$-alkoxy-$C_1$-$C_4$-alkyl, $C_1$-$C_8$-alkylthio, $C_1$-$C_6$-halogenoalkyl, $C_1$-$C_6$-halogenalkoxy or $C_1$-$C_6$-halogenoalkylthio, substituted or non substituted $C_1$-$C_4$-alkoxy-phenyl like benzyloxy, substituted or non substituted phenoxy, substituted, non substituted alkylamino-$C_1$-$C_8$—$NR^7R^8$, substituted, non substituted $NR^7R^8$, $C_1$-$C_8$-alkyl-$S(O)_nR^9$, —$S(O)_nR^9$, $C_1$-$C_8$-alkyl-$SO_2NR^7R^3$, —$SO_2NR^7R^8$, $C_1$-$C_8$-alkyl-$C(O)R^{10}$, —$CR^9$=N—O—$R^{11}$;

two substituents $R^6$ may form a carbocyclic or heterocyclic ring, which may comprise one or more heteroatoms selected in the list consisting of O, N, S;

n represents 0, 1 or 2;

$R^7$ and $R^8$, which may the same or different, represent H, substituted or non-substituted $C_1$-$C_6$-alkyl;

$R^7$ and $R^3$ may form a heterocyclic ring, which may comprise one or more heteroatoms selected in the list consisting of O, N, S;

$R^9$ represents H, substituted or non-substituted, linear or branched $C_1$-$C_8$-alkyl, $C_1$-$C_8$-alkenyl, $C_1$-$C_8$-alkinyl;

$R^{10}$ represents H, substituted or non-substituted, linear or branched $C_1$-$C_8$-alkyl, $C_1$-$C_8$-alkoxy, $NR^7R^8$;

$R^{11}$ represents H, substituted or non-substituted, linear or branched $C_1$-$C_8$-alkyl, $C_1$-$C_4$-alkyl-phenyl, $C_1$-$C_4$-alkoxy-$C_1$-$C_4$-alkyl, substituted or non-substituted $C_1$-$C_4$-alkyl-phenyl, substituted or non-substituted phenyl;

$R^9$ and $R^{11}$ may form a heterocyclic ring, which may comprise one or more heteroatoms selected in the list consisting of O, N, S;

as well as salts, N-oxydes, metallic complexes, metalloidic complexes and optically active or geometric isomers thereof.

BRIEF DESCRIPTION OF THE DRAWINGS

FIG. 1 shows the structure of formula I.

DETAILED DESCRIPTION OF A PREFERRED EMBODIMENT

Any of the compounds according to the invention can exist in one or more optical, geometric or chiral isomer forms depending on the number of asymmetric centres in the compound. The invention thus relates equally to all the optical isomers and to their racemic or scalemic mixtures (the term "scalemic" denotes a mixture of enantiomers in different proportions), and to the mixtures of all the possible stereoisomers, in all proportions. The diastereoisomers and/or the optical isomers can be separated according to the methods which are known per se by the man ordinary skilled in the art.

Any of the compounds according to the invention can also exist in one or more geometric isomer forms depending on the number of double bonds in the compound. The invention thus relates equally to all geometric isomers and to all possible mixtures, in all proportions. The geometric isomers can be separated according to general methods, which are known per se by the man ordinary skilled in the art.

For the compounds according to the invention, halogen means either one of fluorine, bromine, chlorine or iodine and heteroatom can be nitrogen, oxygen or sulphur.

Preferred compounds of formula (I) according to the invention are those wherein $R^1$ represents H; $C_1$-$C_{12}$-alkyl, preferably $C_1$-$C_{12}$-alkyl like methyl; or SH.

Other preferred compounds of formula (I) according to the invention are those wherein $R^2$ represents methyl.

Still other preferred compounds of formula (I) according to the invention are those wherein $R^3$ represents $C_2$-$C_{12}$-alkyl, preferably a non substituted $C_2$-$C_4$-alkyl like ethyl, n-propyl, i-propyl $C_2$-$C_{12}$-alkenyl, preferably $C_3$-$C_4$-alkenyl like propenyl or allyl; $C_3$-$C_6$-cycloalkyl like cyclopropyl.

Still other preferred compounds of formula (I) according to the invention are those wherein $R^2$ and $R^3$ can form together a substituted or non substituted 5 to 7-membered heterocycle, preferably a 6-membered heterocycle, more preferably a pipiridinyl or a pyrrolidinyl, even more preferably a 2-alkylated-pyrrolidinyl like a 2-methyl-pyrrolidinyl.

Still other preferred compounds of formula (I) according to the invention are those wherein $R^4$ represents a $C_1$-$C_{12}$-alkyl, preferably a non substituted $C_1$-$C_{12}$-alkyl like methyl and ethyl; a halogen atom like a fluorine and a chlorine atom; trifluoromethyl.

Still other preferred compounds of formula (I) according to the invention are those wherein $R^5$ represents a H, $C_1$-$C_{12}$-alkyl, preferably a non substituted $C_1$-$C_{12}$-alkyl like methyl and ethyl; a halogen atom like a fluorine and a chlorine atom; trifluoromethyl.

Still other preferred compounds of formula (I) according to the invention are those wherein m represents 1, 2, 3 or 4; even more preferably m represents 1, 2 or 3.

Still other preferred compounds of formula (I) according to the invention are those wherein $R^6$, which may be the same or different, represents H; F, Cl, Br, I; nitro; cyano; $C_1$-$C_6$-alkyl; $C_1$-$C_4$-alkyl-phenyl which may be non substituted or substituted by halogen, $C_1$-$C_4$-alkyl or $C_1$-$C_4$-halogenoalkyl; phenyl which may be non substituted or substituted by halogen, $C_1$-$C_4$-alkyl or $C_1$-$C_4$-halogenoalkyl; $C_1$-$C_6$-alkoxy; $C_1$-$C_4$-alkoxy-$C_1$-$C_4$-alkyl; $C_1$-$C_6$-alkylthio; $C_1$-$C_6$-halogenoalkyl; $C_1$-$C_6$-halogenalkoxy; $C_1$-$C_6$-halogenoalkylthio; $C_1$-$C_6$-alkoxy; $C_1$-$C_4$-alkoxy-$C_1$-$C_4$-alkyl; $C_1$-$C_6$-alkylthio; benzyloxy which may be non substituted or substituted by halogen; phenoxy which may be non substituted or substituted by a halogen atom or $CF_3$; $NR^7R^8$; $C_1$-$C_4$-alkyl-$NR^7R^8$; $S(O)_nR^9$; $C_1$-$C_4$-alkyl-$S(O)_nR^9$; $OR^{10}$; $C_1$-$C_4$-alkyl-$COR^{10}$; —$CR^9$=N—O—$R^{11}$.

Still other preferred compounds of formula (I) according to the invention are those wherein $R^7$ and $R^8$ which may be the same or different, represent H, $C_1$-$C_6$ alkyl or $R^7$ and $R^8$ may form a heterocyclic ring comprising further heteroatoms selected in the list consisting of O, S, N.

Still other preferred compounds of formula (I) according to the invention are those wherein $R^9$ represents H, methyl or ethyl.

Still other preferred compounds of formula (I) according to the invention are those wherein $R^{10}$ represents H; $C_1$-$C_4$-alkyl; $C_1$-$C_4$-alkoxy; $NR^7R^8$.

Still other preferred compounds of formula (I) according to the invention are those wherein $R^{11}$ represents H; $C_1$-$C_4$-alkyl; $C_1$-$C_4$-halogenoalkyl; $C_1$-$C_4$-alkyl-phenyl wherein phenyl may substituted by F, Cl, Br, I, $C_1$-$C_4$-alkyl, $C_1$-$C_4$-halogenoalkyl or $C_1$-$C_4$-halogenoalkoxy; $C_1$-$C_4$-alkoxy-$C_1$-$C_4$-alkyl; phenoxy; benzyloxy.

Still other preferred compounds of formula (I) according to the invention are those wherein $R^9$ and $R^{11}$ may form a 5- or 6-membered heterocyclic ring comprising a further heteroatoms selected in the list consisting of O, S, N.

The above mentioned preferences with regard to the substituents of the compounds according to the invention can be combined in various manners. These combinations of preferred features thus provide sub-classes of compounds according to the invention. Examples of such sub-classes of preferred compounds according to the invention can combine:

preferred features of $R^1$ with preferred features of $R^2$ to $R^6$ or to $R^{11}$ where applicable;

preferred features of $R^2$ with preferred features of $R^1$ to $R^6$ or to $R^{11}$ where applicable;

preferred features of $R^3$ with preferred features of $R^1$ to $R^6$ or to $R^{11}$ where applicable;

preferred features of $R^4$ with preferred features of $R^1$ to $R^6$ or to $R^{11}$ where applicable;

preferred features of $R^5$ with preferred features of $R^1$ to $R^6$ or to $R^{11}$ where applicable.

In these combinations of preferred features of the substituents of the compounds according to the invention, the said preferred features can also be selected among the more preferred features of each of m, n and $R^1$ to $R^{11}$ so as to form most preferred subclasses of compounds according to the invention.

The present invention also relates to a process for the preparation of a compound of formula (I). Generally, the preparation of compound of formula (I) according to the invention can be carried out as illustrated by scheme 1.

Scheme 1
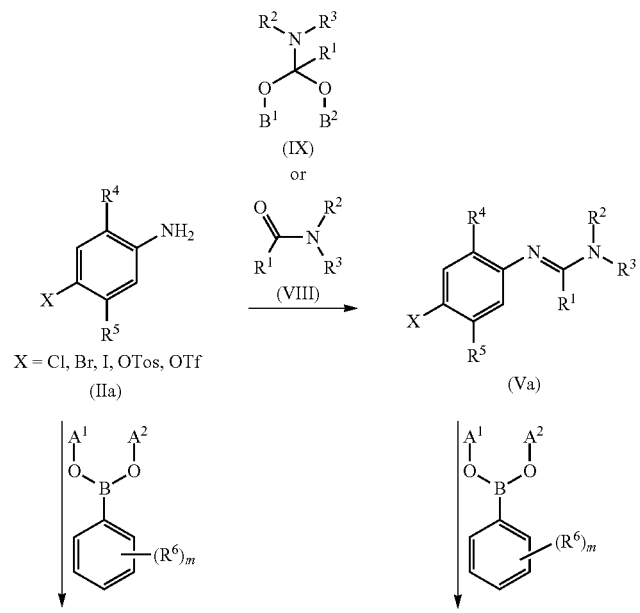
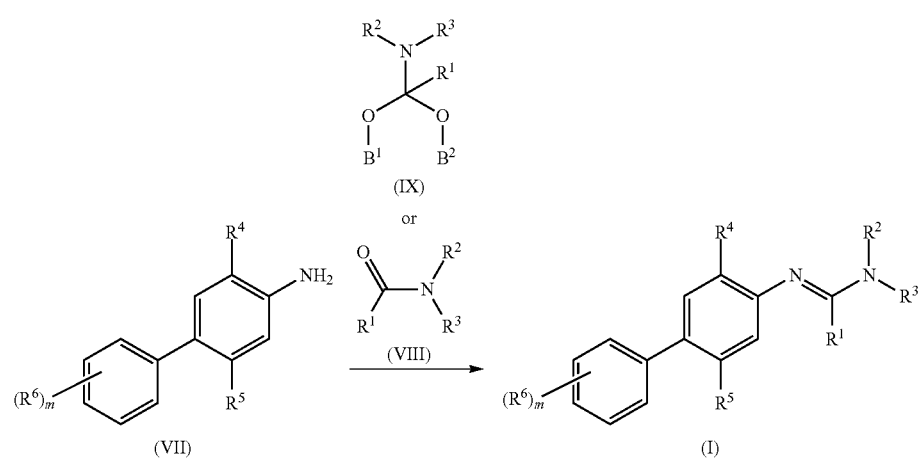

Thus according to a further aspect according to the invention, there is provided a process (a) for the preparation of aniline derivatives of formulae (I) or (VII) by reacting aniline derivatives of formulae (IIa) or (Va)

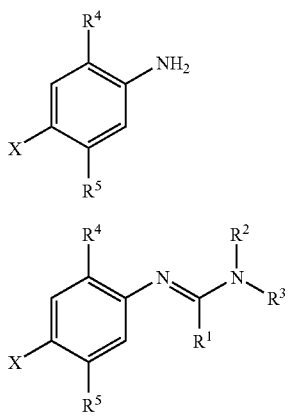

(IIa)

(Va)

wherein

R¹, R², R³, R⁴ and R⁵ are as herein-defined and

X represents halogen, tosylate, SOMe, mesylate or triflate:

with a boronic acid derivative of formula (IV)

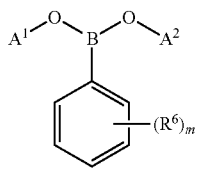

(IV)

wherein m and R⁶ are as herein-defined

A¹ and A² are each represent hydrogen or together represent tetramethylethylene.

Process (a) according to the invention can further comprise one or more of the following characteristics:

presence of an acid binder;

presence of an inert organic diluent;

presence of a catalyst.

Process (a) according to the invention is carried out using 2,3-dimethyl-4-bromo-aniline and 4-tert-butyl-phenyl-boronic acid as starting materials and a catalyst. Process (a) can be conducted according to scheme 2:

Scheme 2

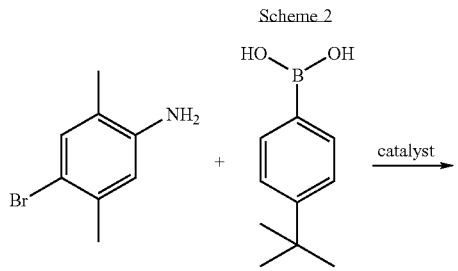

-continued

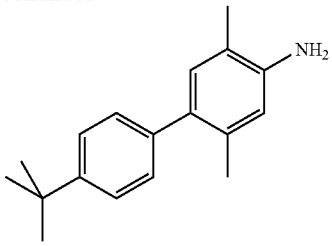

For carrying out process (a) according to the invention, aniline or amidine derivatives of formulae (IIa) or (Va) respectively are used as starting materials.

Preferred starting materials for process (a) according to the invention are compounds of formulae (IIa) or (Va) wherein R¹, R², R³, R⁴ and R⁵ represent substituents as herein-defined for preferred compound of formula (I) according to the invention.

X represents halogen, triflate, SOMe, mesylate, tosylate.

Aniline derivatives of formula (IIa) and boronic acid derivatives of formula (IV), as well as respective process for their preparation are known.

Formula (IV) provides a general definition of the boronic acid derivatives furthermore required as starting materials for carrying out process (a) according to the invention. In formula (IV), R⁶ and m represent preferably substituents which have already been described as preferred in connection with compound of formula (I) A¹ and A² preferably each represent hydrogen or together represent tetramethylethylene for compound of formula (IV).

Boronic acid derivatives of formula (IV) are known and can be prepared by known processes, for example described in WO-01/90084 or U.S. Pat. No. 5,633,218. These derivatives can be obtained, for example, by reacting a phenyl derivative of formula (VI)

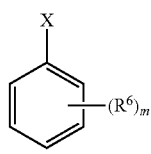

(VI)

wherein R⁶, and m are as herein-defined, X represents halogen, triflate, SOMe, mesylate, tosylate; with boric acid esters of formula (XI)

B(O-Alk)₃  (XI)

wherein Alk represents C₁-C₄-alkyl; or with 4,4,4',4',5,5,5',5'-octamethyl-2,2'-bis-1,3,2-dioxaborolane; in the presence of magnesium or alkyllithium. A diluent like tetrahydrofuran can be used.

Formula (XI) provides a general definition of the boric acid esters that can be used for preparing boronic acid derivatives of formula (IV) according to the invention. In formula (XI), Alk preferably represents methyl, ethyl, n- or iso-propyl, more preferably methyl or ethyl. Boric acid esters of formula (XI) are known compounds.

A further aspect according to the invention lies in a process (b) for the preparation of aniline derivatives of formulae (I) or (VII) by reacting boronic acid derivatives of formulae (IIb) or (Vb)

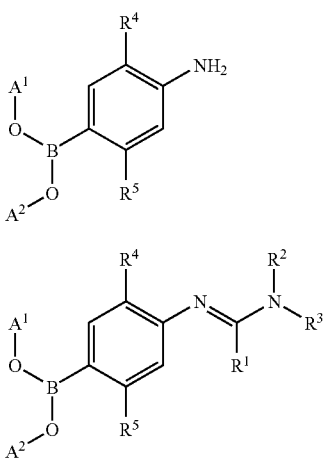

wherein
R¹, R², R³, R⁴ and R⁵ are as herein-defined and
A¹ and A² each represent hydrogen or together represent tetramethylethylene;
with phenyl derivatives of formula (VI)

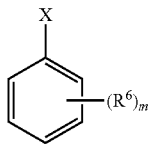

wherein
R⁶ and m are as herein-defined
X represents halogen, triflate, SOMe, mesylate, tosylate.
Process (b) according to the invention can further comprise one or more of the following characteristics:
presence of an acid binder;
presence of an inert organic diluent;
presence of a catalyst.
A further aspect according to the invention lies in a process (c) for the preparation of aniline derivatives of formulae (I) or (VII) by reacting aniline derivatives of formulae (IIa) or (Va)

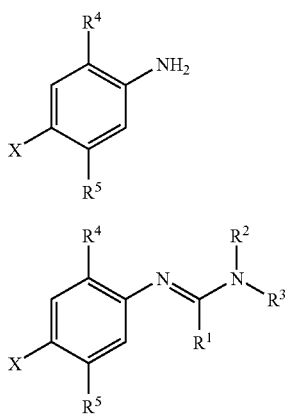

wherein
R¹, R², R³, R⁴ and R⁵ are as herein-defined and
X represents halogen, triflate, SOMe, mesylate, tosylate;
with phenyl derivatives of the formula (VI)

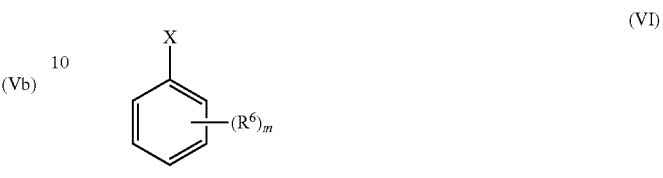

wherein
R⁶ and m are as herein-defined;
X represents halogen, triflate, SOMe, mesylate, tosylate;
in the presence of a palladium, nickel or platinum catalyst and in the presence of 4,4,4',4',5,5,5',5'-octamethyl-2,2'-bis-1,3,2-dioxaborolane.

Process (c) according to the invention can further comprise one or more of the following characteristics:
presence of an acid binder;
presence of an inert organic diluent.

Formula (IIa) and (Va) provide general definitions of the substituted amine derivatives useful as reaction components for carrying out processes (a) or (c) according to the invention. In these formulae, R¹, R², R³, R⁴ and R⁵ preferably represent substituents as herein-defined in connection with the description of compounds of formula (I) according to the invention. Halogen preferably represents chlorine, bromine or iodine, more preferably bromine or iodine.

Aniline derivatives of formula (II) are known compounds and can be prepared by known methods from the corresponding nitro compounds by reduction, or by halogenation of the corresponding aniline derivatives.

The boronic acid derivatives of formula (IV) that can be used as starting materials for carrying out process (a) according to the invention are known or commercially available reagents.

Formulae (IIb) and (Vb) provide general definitions of the boronic acid derivatives useful as reaction components for carrying out process (b) according to the invention. In these formulae R¹, R², R³, R⁴ and R⁵ preferably represent substituents as herein-defined in connection with the description of compounds of formula (I) according to the invention. A¹ and A² preferably each represent hydrogen or together represent tetramethylethylene.

Boronic acid derivatives of formula (IIb), (Vb) or phenyl derivatives of formula (VI) are known and can be prepared by known methods.

Amidine derivatives of formulae (I) and (Va) can be obtained by a further process according to the invention. Various alternatives of process (d) according to the invention can be considered, they are defined as process (d1), process (d2) and process (d3) according to the invention. Process (d) according to the invention comprises reacting aniline derivatives of formulae (VII) or (IIa) with different reagents thus defining processes (d1), (d2) and (d3) respectively

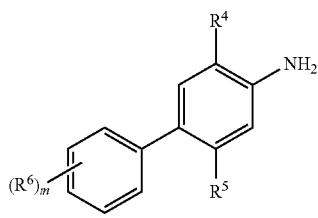
(VII)

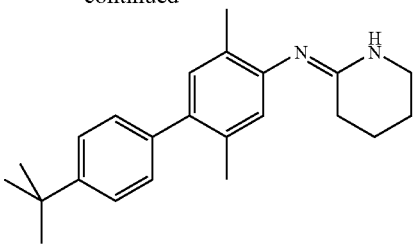

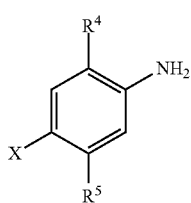
(IIa)

wherein $R^4$, $R^5$, $R^5$, $R^6$ and m are as herein-defined

X represents halogen, triflate, SOMe, mesylate or tosylate.

Process (d1) is carried out further using amide derivatives of formula (VIII)

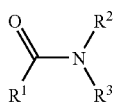
(VIII)

wherein $R^1$, $R^2$, $R^3$ are as herein-defined.

Process (d1) according to the invention can further comprise one or more of the following characteristics:

presence of a halogenation agent, like $PCl_5$, $PCl_3$, $POCl_3$, $SOCl_2$;

presence of a dilutent.

Process (d1) according to the invention is carried out using 4'-tert-butyl-2,5-dimethylbiphenyl-4-amine, piperidin-2-one and phosphoric trichloride as starting materials and an acid. Process (d1) can be conducted according to scheme 3.

Scheme 3

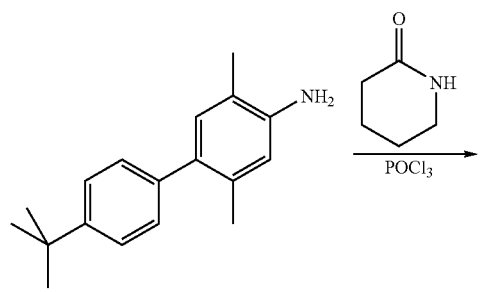

Formula (VII) provides a general definition of the biphenylamines useful as starting materials for carrying out the process (d1) according to the invention. In this formula $R^1$, $R^2$, $R^3$, $R^4$, $R^5$, $R^6$ and m preferably represent substituents or values as herein-defined in connection with the description of compounds of formula (I) according to the invention.

Process (d2) is carried out further using amino-acetal derivatives of formula (IX)

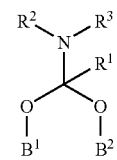
(IX)

wherein $R^1$, $R^2$, $R^3$ are as herein-defined $B^1$ and $B^2$ represent each alkyl or together cycloalkyl.

Process (d2) according to the invention can further comprise one or more of the following characteristics:

presence of a acid or base;

presence of a dilutent.

Process (d2) according to the invention is carried out using 4'-tert-butyl-2,5-dimethylbiphenyl-4-amine and N-(dimethoxymethyl)-N-methylethanamine as starting materials. Process (d2) can be conducted according to scheme 4.

Scheme 4

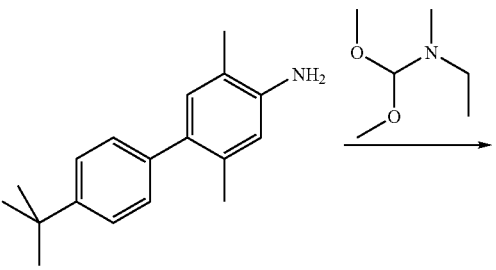

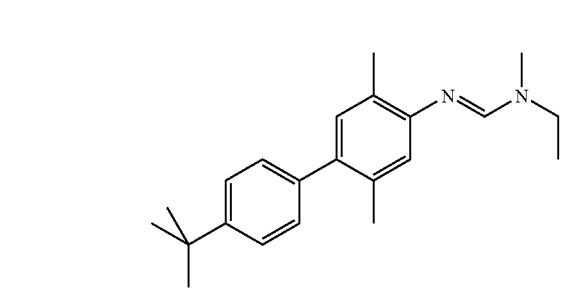

Process (d3) is carried out further using amine derivatives of formula (X)

(X)

wherein
R² and R³ are as herein-defined;
in presence of orthoester derivatives of formula (XI)

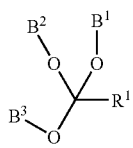
(XI)

wherein
R¹ is as herein-defined;
B¹, B² and B³ represent each alkyl.

Formula (VII) provides a general definition of the biphenylamines useful as starting materials for carrying out process (d3) according to the invention. In this formula R¹, R², R³, R⁴, R⁵, R⁶ and m preferably represent substituents or values as herein-defined in connection with the description of compounds of formula (I) according to the invention.

Process (d3) according to the invention is carried out using 4'-tert-butyl-2,5-dimethylbiphenyl-4-amine, trimethyl-ortho-ester and N-methyl-ethanamine as starting materials and an acid. Process (d3) can be conducted according to scheme 5.

Scheme 5

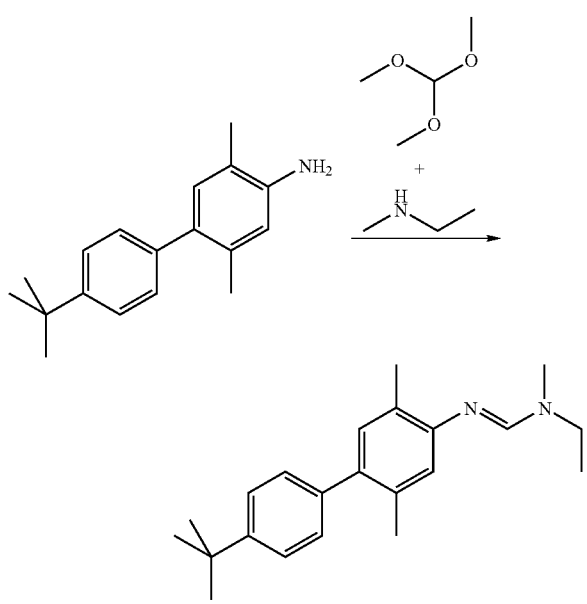

Formula (VII) provides a general definition of the biphenylamines useful as starting materials for carrying out the process (d3) according to the invention. In this formula R¹, R², R³, R⁴, R⁵, R⁶ and m preferably represent substituents or values as herein-defined in connection with the description of compounds of formula (I) according to the invention.

Processes (d), (d1), (d2) or (d3) according to the invention can further comprise one or more of the following characteristics:
presence of a acid or base;
presence of a dilutent.

Suitable diluents for carrying out the processes (a), (b) and (c) according to the invention are all customary inert organic solvents. Preference is given to using aliphatic, alicyclic or aromatic hydrocarbons, such as petroleum ether, hexane, heptane, cyclohexane, methylcyclohexane, benzene, toluene, xylene or decalin; halogenated hydrocarbons, such as chlorobenzene, dichlorobenzene, dichloromethane, chloroform, carbon tetrachloride, dichloroethane or trichloroethane; ethers, such as diethyl ether, diisopropyl ether, methyl tert-butyl ether, methyl tert-amyl ether, dioxane, tetrahydrofuran, 1,2-dimethoxyethane, 1,2-diethoxyethane or anisole; nitriles, such as acetonitrile, propionitrile, n- or iso-butyronitrile or benzonitrile; amides, such as N,N-dimethylformamide, N,N-dimethylacetamide, N-methylformanilide, N-methylpyrrolidone or hexamethylphosphoric triamide; mixtures thereof with water or pure water.

Suitable diluents for carrying out the processes (d1), (d2) and (d3) according to the invention are in each case all customary inert organic solvents. Preference is given to using aliphatic, alicyclic or aromatic hydrocarbons, such as petroleum ether, hexane, heptane, cyclohexane, methylcyclohexane, benzene, toluene, xylene or decalin; ethers, such as diethyl ether, diisopropyl ether, methyl tert-butyl ether, methyl tert-amyl ether, dioxane, tetrahydrofuran, 1,2-dimethoxyethane, 1,2-diethoxyethane or anisole; nitriles, such as acetonitrile, propionitrile, n- or iso-butyronitrile or benzonitrile; amides, such as N,N-dimethylformamide, N,N-dimethylacetamide, N-methylformanilide, N-methylpyrrolidone or hexamethylphosphoric triamide; esters, such as methyl acetate or ethyl acetate; sulphoxides, such as dimethylsulphoxide; or sulphones, such as sulpholane; alcohols, such as methanol, ethanol, n- or iso-propanol, n-, iso-, sec- or tert-butanol, ethanediol, propane-1,2-diol, ethoxyethanol, methoxyethanol, diethyleneglycolmonomethylether, diethyleneglycolmonoethylether; mixtures thereof with water or pure water.

Suitable acid binders for carrying out the processes (a), (b) and (c) according to the invention are all inorganic and organic bases customary for such reactions. Preference is given to using alkaline earth metal or alkali metal hydrides, hydroxides, amides, alcoholates, acetates, carbonates or hydrogen carbonates, such as sodium hydride, sodium amide, lithium diisoproylamide, sodium methanolate, sodium ethanolate, potassium tert-butanolate, sodium acetate, potassium acetate, calcium acetate, sodium hydroxide, potassium hydroxide, sodium carbonate, potassium carbonate, potassium bicarbonate, sodium bicarbonate, or ammonium carbonate; and also tertiary amines, such as trimethylamine, triethylamine, tributylamine, N,N-dimethylaniline, N,N-dimethyl-benzylamine pyridine, N-methylpiperidine, N-methylmorpholine, N,N-dimethylaminopyridine, diazabicyclooctane (DABCO), diazabicyclononene (DBN) or di-azabicycloundecene (DBU).

Suitable acid binders for carrying out the processes (b), (c), (d) according to the invention are in each case all inorganic and organic bases customary for such reactions. Preference is given to using alkaline earth metal or alkali metal hydrides, hydroxides, amides, alcoholates, acetates, fluorides, phosphates, carbonates or hydrogen carbonates, such as sodium hydride, sodium-amide, lithium diisopropylamide, sodium methanolate, sodium ethanolate, potassium tert-butanolate, sodium hydroxide, potassium hydroxide, sodium acetate, sodium phosphate, potassium phosphate, potassium fluoride, caesium fluoride, sodium carbonate, potassium carbonate, potassium hydrogencarbonate, sodium hydrogencarbonate or caesium carbonate; and also tertiary amines, such as trimethylamine, triethylamine, tributylamine, N,N-dimethylaniline, N,N-dimethyl-benzylamine, pyridine, N-methylpiperidine, N-methylmorpholine, N,N-dimethylaminopyridine, diazabicyclooctane (DABCO), diazabicyclononene (DBN) or diazabicycloundecene (DBU).

Suitable acids for carrying out the process (d3) according to the invention are all inorganic and organic acids customary for such reactions. Preference is given to using para-toluene sulfonic acid, methane sulfonic acid, hydrochloric acid (gas, aqueous or organic solution) or sulphuric acid.

Suitable condensing agents for carrying out the process (d1) according to the invention are all condensing agents customary for such amidation reactions. Preference is given to using acid halide former, such as phosgene, phosphorous tribromide, phosphorous trichloride, phosphorous pentachloride, phosphorous trichloride oxide or thionyl chloride; anhydride former, such as ethyl chloroformate, methyl chloroformate, isopropyl chloroformate, isobutyl chloroformate or methanesulfonyl chloride; carbodiimides, such as N,N'-dicyclohexylcarbodiimide (DCC) or other customary condensing agents, such as phosphorous pentoxide, polyphosphoric acid, N,N'-carbonyldiimidazole, 2-ethoxy-N-ethoxycarbonyl-1,2-dihydroquinoline (EEDQ), triphenylphosphine/tetrachloromethane or bromo-tripyrrolidino-phosphonium-hexafluorophosphate.

Processes (a), (b) and (c) to the invention can be carried out in the presence of a catalyst. Preference is given to palladium salts or complexes, such as palladium chloride, palladium acetate, tetrakis-(triphenylphosphine) palladium, bis-(triphenylphosphine) palladium dichloride or 1,1'-Bis(diphenylphosphino)ferrocenepalladium(II)chloride.

It is also possible to generate a palladium complex directly in the reaction mixture by separately adding to the reaction mixture a palladium salt and a complex ligand, such as triethylphosphane, tri-tert-butylphosphane, tricyclohexylphosphane, 2-(dicyclohexylphosphane)biphenyl, 2-(di-tert-butylphosphan)biphenyl, 2-(dicyclohexylphosphane)-2'-(N,N-dimethylamino)-biphenyl, triphenylphosphane, tris-(o-tolyl) phosphane, sodium 3-(diphenylphosphino)benzolsulfonate, tris-2-(methoxyphenyl)phosphane, 2,2'-bis-(diphenylphosphane)-1,1'-binaphthyl, 1,4-bis-(diphenylphosphane)butane, 1,2-bis-(diphenylphosphane)ethane, 1,4-bis-(dicyclohexylphosphane)butane, 1,2-bis-(dicyclohexylphosphane)ethane, 2-(dicyclohexylphosphane)-2'-(N,N-dimethylamino)-biphenyl, bis(diphenylphosphino)ferrocene or tris-(2,4-tert-butylphenyl)-phosphite.

When carrying out processes (d) according to the invention, the reaction temperature can be varied within a relatively wide range. In general, the process is carried out at temperatures between from 0° C. to 150° C., preferably from 0° C. to 120° C., particularly preferably from 10° C. to 90° C.

When carrying out processes (a), (b), and according to the invention, the reaction temperatures can in each case be varied within a relatively wide range. In general, the processes are carried out at temperatures from 0° C. to 180° C., preferably from 10° C. to 150° C., particularly preferably from 20° C. to 120° C.

When carrying out the process (a) according to the invention, in general 0.5 to 15 mole, preferably from 0.8 to 8 mole, of boronic acid derivative of the formula (IV) and from 1 to 5 mol of acid binder and from 0.2 to 5 mol % of catalyst are employed per mole of amine or amidine of the formula (IIa) or (Va). However, it is also possible to employ the reaction components in other ratios. Work-up is carried out by customary methods. In general, water is added to the reaction mixture and the precipitate is separated off and dried. The residue that remains may, if appropriate, be freed of any impurities that may still be present using customary methods, such as chromatography or recrystallization.

When carrying out the process (b) according to the invention, in general 0.8 to 15 mole, preferably from 0.8 to 8 mole, of phenyl derivative of the formula (VI) and from 1 to 10 mol of acid binder and from 0.5 to 5 mole % of a catalyst are employed per mole of boronic acid derivative of the formula (IIb) or (Vb). However, it is also possible to employ the reaction components in other ratios. Work-up is carried out by customary methods. In general, water is added to the reaction mixture and the precipitate is separated off and dried. The residue that remains may, if appropriate, be freed of any impurities that may still be present using customary methods, such as chromatography or recrystallization.

When carrying out the process (c) according to the invention, in general 0.8 to 15 mole, preferably from 0.8 to 8 mole, of amine or amidine derivative of the formula (IIa) or (Va) and from 0.8 to 15 mole, preferably from 0.8 to 8 mole, of 4,4,4',4',5,5,5',5'-octamethyl-2,2'-bis-1,3,2-dioxaborolane and from 1 to 5 mol of acid binder and from 1 to 5 mol of a catalyst are employed per mole of phenyl derivative of the formula (VI). However, it is also possible to employ the reaction components in other ratios. Work-up is carried out by customary methods. In general, water is added to the reaction mixture and the precipitate is separated off and dried. The residue that remains may, if appropriate, be freed of any impurities that may still be present using customary methods, such as chromatography or recrystallization.

When carrying out process (d1) according to the invention, per mole of the amine of the formula (VII) or (Va) in general 0.8 to 50 mole, preferably 1 to 10 mole of amide of the formula (VIII) and 1 to 10 mole of halogenation agent are employed. However, it is also possible to employ the reaction components in other ratios. Work-up is carried out by customary methods.

When carrying out process (d2) according to the invention, per mole of the amine of the formula (VII) or (Va) in general 0.8 to 50 mole, preferably 1 to 10 mole of an aminoacetal of the formula (IX) are employed. However, it is also possible to employ the reaction components in other ratios. Work-up is carried out by customary methods.

When carrying out process (d3) according to the invention, per mole of the amine of the formula (VII) or (Va) in general 0.8 to 50 mole, preferably 1 to 10 mole of an orthoester of the formula (XI) and 0.8 to 50 mole, preferably 1 to 10 mole of an amine of the formula (X) and a catalytic amount of acid are employed. However, it is also possible to employ the reaction components in other ratios. Work-up is carried out by customary methods.

All processes according to the invention are generally each carried out under atmospheric pressure. However, in each case it is also possible to operate under elevated or reduced pressure—in general between 0.1 bar and 10 bar.

Compounds of formula (I) according to the invention can be prepared according to the herein described processes. It will nevertheless be understood that, on the basis of his general knowledge and of available publications, the skilled worker will be able to adapt these processes according to the specifics of each of the compounds which it is desired to synthesise.

In a further aspect, the present invention also relates to a fungicide or insecticide composition comprising an effective and non-phytotoxic amount of an active compound of formula (I). The expression "effective and non-phytotoxic amount" means an amount of composition according to the invention which is sufficient to control or destroy the fungi present or liable to appear on the crops, and which does not entail any appreciable symptom of phytotoxicity for the said crops. Such an amount can vary within a wide range depending on the fungus to be controlled, the type of crop, the climatic conditions and the compounds included in the fungicide composition according to the invention.

This amount can be determined by systematic field trials, which are within the capabilities of a person skilled in the art.

Thus, according to the invention, there is provided a fungicide or insecticide composition comprising, as an active ingredient, an effective amount of a compound of formula (I) as herein-defined and an agriculturally acceptable support, carrier or filler.

According to the invention, the term "support" denotes a natural or synthetic, organic or inorganic compound with which the active compound of formula (I) is combined or associated to make it easier to apply, notably to the parts of the plant. This support is thus generally inert and should be agriculturally acceptable. The support may be a solid or a liquid. Examples of suitable supports include clays, natural or synthetic silicates, silica, resins, waxes, solid fertilisers, water, alcohols, in particular butanol, organic solvents, mineral and plant oils and derivatives thereof. Mixtures of such supports may also be used.

The composition according to the invention may also comprise additional components. In particular, the composition may further comprise a surfactant. The surfactant can be an emulsifier, a dispersing agent or a wetting agent of ionic or non-ionic type or a mixture of such surfactants. Mention may be made, for example, of polyacrylic acid salts, lignosulphonic acid salts, phenolsulphonic or naphthalenesulphonic acid salts, polycondensates of ethylene oxide with fatty alcohols or with fatty acids or with fatty amines, substituted phenols (in particular alkylphenols or arylphenols), salts of sulphosuccinic acid esters, taurine derivatives (in particular alkyl taurates), phosphoric esters of polyoxyethylated alcohols or phenols, fatty acid esters of polyols, and derivatives of the present compounds containing sulphate, sulphonate and phosphate functions. The presence of at least one surfactant is generally essential when the active compound and/or the inert support are water-insoluble and when the vector agent for the application is water. Preferably, surfactant content may be comprised from 5% to 40% by weight of the composition.

Optionally, additional components may also be included, e.g. protective colloids, adhesives, thickeners, thixotropic agents, penetration agents, stabilisers, sequestering agents. More generally, the active compounds can be combined with any solid or liquid additive, which complies with the usual formulation techniques.

In general, the composition according to the invention may contain from 0.05 to 99% by weight of active compound, preferably 10 to 70% by weight.

Compositions according to the invention can be used in various forms such as aerosol dispenser, bait (ready for use), bait concentrate, block bait, capsule suspension, cold fogging concentrate, dustable powder, emulsifiable concentrate, emulsion oil in water, emulsion water in oil, encapsulated granule, fine granule, flowable concentrate for seed treatment, gas (under pressure), gas generating product, grain bait, granular bait, granule, hot fogging concentrate, macrogranule, microgranule, oil dispersible powder, oil miscible flowable concentrate, oil miscible liquid, paste, plant rodlet, plate bait, powder for dry seed treatment, scrap bait, seed coated with a pesticide, smoke candle, smoke cartridge, smoke generator, smoke pellet, smoke rodlet, smoke tablet, smoke tin, soluble concentrate, soluble powder, solution for seed treatment, suspension concentrate (=flowable concentrate), tracking powder, ultra low volume (ulv) liquid, ultra low volume (ulv) suspension, vapour releasing product, water dispersible granules or tablets, water dispersible powder for slurry treatment, water soluble granules or tablets, water soluble powder for seed treatment and wettable powder.

These compositions include not only compositions which are ready to be applied to the plant or seed to be treated by means of a suitable device, such as a spraying or dusting device, but also concentrated commercial compositions which must be diluted before application to the crop.

The compounds according to the invention can also be mixed with one or more insecticide, fungicide, bactericide, attractant, acaricide or pheromone active substance or other compounds with biological activity. The mixtures thus obtained have a broadened spectrum of activity.

The mixtures with other fungicide compounds are particularly advantageous. Examples of suitable fungicide mixing partners may be selected in the following lists:

B1) a compound capable to inhibit the nucleic acid synthesis like benalaxyl, benalaxyl-M, bupirimate, chiralaxyl, clozylacon, dimethirimol, ethirimol, furalaxyl, hymexazol, metalaxyl, metalaxyl-M, ofurace, oxadixyl, oxolinic acid;

B2) a compound capable to inhibit the mitosis and cell division like benomyl, carbendazim, diethofencarb, fuberidazole, pencycuron, thiabendazole thiophanate-methyl, zoxamide;

B3) a compound capable to inhibit the respiration for example as CI-respiration inhibitor like diflumetorim;
as CII-respiration inhibitor like boscalid, carboxin, fenfuram, flutolanil, furametpyr, mepronil, oxycarboxine, penthiopyrad, thifluzamide;
as CIII-respiration inhibitor like azoxystrobin, cyazofamid, dimoxystrobin, enestrobin, famoxadone, fenamidone, fluoxastrobin, kresoxim-methyl, metominostrobin, orysastrobin, pyraclostrobin, picoxystrobin, trifloxystrobin;

B4) a compound capable of to act as an uncoupler like dinocap, fluazinam;

B5) a compound capable to inhibit ATP production like fentin acetate, fentin chloride, fentin hydroxide, silthiofam;

B6) a compound capable to inhibit AA and protein biosynthesis like andoprim, blasticidin-S, cyprodinil, kasugamycin, kasugamycin hydrochloride hydrate, mepanipyrim, pyrimethanil;

B7) a compound capable to inhibit the signal transduction like fenpiclonil, fludioxonil, quinoxyfen;

B8) a compound capable to inhibit lipid and membrane synthesis like chlozolinate, iprodione, procymidone, vinclozolin, pyrazophos, edifenphos, iprobenfos (IBP), isoprothiolane, tolclofos-methyl, biphenyl, iodocarb, propamocarb, propamocarb-hydrochloride;

B9) a compound capable to inhibit ergosterol biosynthesis like fenhexamid, azaconazole, bitertanol, bromuconazole, cyproconazole, diclobutrazole, difenoconazole, diniconazole, diniconazole-M, epoxiconazole, etaconazole, fenbuconazole, fluquinconazole, flusilazole, flutriafol, furconazole, furconazole-cis, hexaconazole, imibenconazole, ipconazole, metconazole, myclobutanil, paclobutrazol, penconazole, propiconazole, prothioconazole, simeconazole, tebuconazole, tetraconazole, triadimefon, triadimenol, triticonazole, uniconazole, voriconazole, imazalil, imazalil sulfate, oxpoconazole, fenarimol, flurprimidol, nuarimol, pyrifenox, triforine, pefurazoate, prochloraz, triflumizole, viniconazole, aldimorph, dodemorph, dodemorph acetate, fenpropimorph, tridemorph, fenpropidin, spiroxamine, naftifine, pyributicarb, terbinafine;

B10) a compound capable to inhibit cell wall synthesis like benthiavalicarb, bialaphos, dimethomorph, flumorph, iprovalicarb, polyoxins, polyoxorim, validamycin A;

B11) a compound capable to inhibit melanine biosynthesis like carpropamid, diclocymet, fenoxanil, phtalide, pyroquilon, tricyclazole;

B12) a compound capable to induce a host defence like acibenzolar-S-methyl, probenazole, tiadinil;

B13) a compound capable to have a multisite action like captafol, captan, chlorothalonil, copper preparations such as copper hydroxide, copper naphthenate, copper oxychloride, copper sulphate, copper oxide, oxine-copper and Bordeaux mixture, dichlofluanid, dithianon, dodine, dodine free base, ferbam, fluorofolpet, folpet, guazatine, guazatine acetate, iminoctadine, iminoctadine albesilate, iminoctadine triacetate, mancopper, mancozeb, maneb, metiram, metiram zinc, propineb, sulphur and sulphur preparations including calcium polysulphide, thiram, tolylfluanid, zineb, ziram;

B14) a compound selected in the following list: amibromdole, benthiazole, bethoxazin, capsimycin, carvone, chinomethionat, chloropicrin, cufraneb, cyflufenamid, cymoxanil, dazomet, debacarb, diclomezine, dichlorophen, dicloran, difenzoquat, difenzoquat methylsulphate, diphenylamine, ethaboxam, ferimzone, flumetover, flusulfamide, fosetyl-aluminium, fosetyl-calcium, fosetyl-sodium, fluopicolide, fluoroimide, hexachlorobenzene, 8-hydroxyquinoline sulfate, irumamycin, methasulphocarb, metrafenone, methyl isothiocyanate, mildiomycin, natamycin, nickel dimethyldithiocarbamate, nitrothal-isopropyl, octhilinone, oxamocarb, oxyfenthiin, pentachlorophenol and salts, 2-phenylphenol and salts, phosphorous acid and its salts, piperalin, propanosine-sodium, proquinazid, pyrrolnitrine, quintozene, tecloftalam, tecnazene, triazoxide, trichlamide, zanilamid and 2,3,5,6-tetrachloro-4-(methylsulfonyl)-pyridine, N-(4-Chloro-2-nitrophenyl)-N-ethyl-4-methyl-benzenesulfonamide, 2-amino-4-methyl-N-phenyl-5-thiazolecarboxamide, 2-chloro-N-(2,3-dihydro-1,1,3-trimethyl-1H-inden-4-yl)-3-pyridincarboxamide, 3-[5-(4-chlorophenyl)-2,3-dimethylisoxazolidin-3-yl]pyridine, cis-1-(4-chlorophenyl)-2-(1H-1,2,4-triazole-1-yl)-cycloheptanol, methyl 1-(2,3-dihydro-2,2-dimethyl-1H-inden-1-yl)-1H-imidazole-5-carboxylate, 3,4,5-trichloro-2,6-pyridinedicarbonitrile, Methyl 2-[[[cyclopropyl[(4-methoxyphenyl)imino]methyl]thio]methyl]-.alpha.-(methoxymethylene)-benzeneacetate, 4-Chloro-alpha-propynyloxy-N-[2-[3-methoxy-4-(2-propynyloxy)phenyl]ethyl]-benzeneacetamide, (2S)—N-[2-[4-[[3-(4-chlorophenyl)-2-propynyl]oxy]-3-methoxyphenyl]ethyl]-3-methyl-2-[(methylsulfonyl) amino]-butanamide, 5-chloro-7-(4-methylpiperidin-1-yl)-6-(2,4,6-trifluorophenyl)[1,2,4]triazolo[1,5-a] pyrimidine, 5-chloro-6-(2,4,6-trifluorophenyl)-N-[(1R)-1,2,2-trimethylpropyl][1,2,4]triazolo[1,5-a] pyrimidin-7-amine, 5-chloro-N-[(1R)-1,2-dimethylpropyl]-6-(2,4,6-trifluorophenyl)[1,2,4] triazolo[1,5-a]pyrimidin-7-amine, N-[1-(5-bromo-3-chloropyridin-2-yl)ethyl]-2,4-dichloronicotinamide, N-(5-bromo-3-chloropyridin-2-yl)methyl-2,4-dichloronicotinamide, 2-butoxy-6-iodo-3-propyl-benzopyranon-4-one, N-{(Z)-[(cyclopmopylmethoxy)imino][6-(difluoromethoxy)-2,3-difluomophenyl]methyl}-2-phenylacetamide, N-(3-ethyl-3,5,5-trimethylcyclohexyl)-3-formylamino-2-hydroxy-benzamide, 2-[[[[1-[3(1 Fluoro-2-phenylethyl)oxy]phenyl]ethylidene]amino]oxy]methyl]-alpha-(methoxyimino)-N-methyl-alphaE-benzeneacetamide, N-{2-[3-chloro-5-(trifluoromethyl)pyridin-2-yl]ethyl}-2-(trifluoromethyl)benzamide, N-(3',4'-dichloro-5-fluorobiphenyl-2-yl)-3-(difluoromethyl)-1-methyl-1H-pyrazole-4-carboxamide, 2-(2-{[6-(3-chloro-2-methylphenoxy)-5-fluoropyrimidin-4-yl]oxy}phenyl)-2-(methoxyimino)-N-methylacetamide, 1-[(4-methoxyphenoxy)methyl]-2,2-dimethylpropyl-1H-imidazole-1-carboxylic acid, O-[1-[(4-methoxyphenoxy)methyl]-2,2-dimethylpropyl]-1H-imidazole-1-carbothioic acid.

The composition according to the invention comprising a mixture of a compound of formula (I) with a bactericide compound may also be particularly advantageous. Examples of suitable bactericide mixing partners may be selected in the following list: bronopol, dichlorophen, nitrapyrin, nickel dimethyldithiocarbamate, kasugamycin, octhilinone, furancarboxylic acid, oxytetracycline, probenazole, streptomycin, tecloftalam, copper sulphate and other copper preparations.

The compound of formula (I) and the fungicide composition according to the invention can be used to curatively or preventively control the phytopathogenic fungi of plants or crops. Thus, according to a further aspect of the invention, there is provided a method for curatively or preventively controlling the phytopathogenic fungi of plants or crops characterised in that a compound of formula (I) or a fungicide composition according to the invention is applied to the seed, the plant or to the fruit of the plant or to the soil wherein the plant is growing or wherein it is desired to grow.

In the same manner, the compound of formula (I) and the insecticide composition according to the invention can be used to curatively or preventively control damaging insects, notably of plants or crops. Thus, according to a further aspect of the invention, there is provided a method for curatively or preventively controlling damaging insects, notably of plants or crops, characterised in that a compound of formula (I) or an insecticide composition according to the invention is applied to the seed, the plant or to the fruit of the plant or to the soil wherein the plant is growing or wherein it is desired to grow.

The methods of treatment according to the invention may also be useful to treat propagation material such as tubers or rhizomes, but also seeds, seedlings or seedlings pricking out and plants or plants pricking out. These methods of treatment can also be useful to treat roots. The methods of treatment according to the invention can also be useful to treat the overground parts of the plant such as trunks, stems or stalks, leaves, flowers and fruit of the concerned plant. Among the plants that can be protected by the method according to the invention, mention may be made of cotton; flax; vine; fruit or vegetable crops such as Rosaceae sp. (for instance pip fruit such as apples and pears, but also stone fruit such as apricots, almonds and peaches), Ribesioidae sp., Juglandaceae sp., Betulaceae sp., Anacardiaceae sp., Fagaceae sp., Moraceae sp., Oleaceae sp., Actimidaceae sp., Lauraceae sp., Musaceae sp. (for instance banana trees and plantins), Rubiaceae sp., Theaceae sp., Sterculiceae sp., Rutaceae sp. (for instance lemons, oranges and grapefruit); Solanaceae sp. (for instance tomatoes), Liliaceae sp., Asteraceae sp. (for instance lettuces), Umbelliferae sp., Cruciferae sp., Chenopodiaceae sp., Cucurbitaceae sp., Papilionaceae sp. (for instance peas), Rosaceae sp. (for instance strawberries); major crops such as Graminae sp. (for instance maize, lawn or cereals such as wheat, rice, barley and triticale), Asteraceae sp. (for instance sunflower), Cruciferae sp. (for instance colza), Fabacae sp. (for instance peanuts), Papilionaceae sp. (for instance soybean), Solanaceae sp. (for instance potatoes), Chenopodiaceae sp. (for instance beetroots) horticultural and forest crops; as well as genetically modified homologues of these crops.

Among the diseases of plants or crops that can be controlled by the method according to the invention, mention may be made of:

Powdery mildew diseases such as:
Blumeria diseases, caused for example by *Blumeria graminis*;
Podosphaera diseases, caused for example by *Podosphaera leucotricha*;
Sphaerotheca diseases, caused for example by *Sphaerotheca fuliginea*;
Uncinula diseases, caused for example by *Uncinula necator*;
Rust diseases such as:
Gymnosporangium diseases, caused for example by *Gymnosporangium sabinae*;
Hemileia diseases, caused for example by *Hemileia vastatrix*;
Phakopsora diseases, caused for example by *Phakopsora pachyrhizi* or *Phakopsora* meibomiae;
Puccinia diseases, caused for example by *Puccinia recondita*;
Uromyces diseases, caused for example by *Uromyces appendiculatus*;
Oomycete diseases such as:
Bremia diseases, caused for example by *Bremia lactucae*;
Peronospora diseases, caused for example by *Peronospora pisi* or *P. brassicae*;
Phytophthora diseases, caused for example by *Phytophthora infestans*;
Plasmopara diseases, caused for example by *Plasmopara viticola*;
Pseudoperonospora diseases, caused for example by *Pseudoperonospora humuli* or
*Pseudoperonospora cubensis*;
Pythium diseases, caused for example by *Pythium ultimum*;
Leafspot, leaf blotch and leaf blight diseases such as:
Alternaria diseases, caused for example by *Alternaria solani*;
Cercospora diseases, caused for example by *Cercospora beticola*;
Cladiosporum diseases, caused for example by *Cladiosporium cucumerinum*;
Cochliobolus diseases, caused for example by *Cochliobolus sativus*;
Colletotrichum diseases, caused for example by *Colletotrichum lindemuthianum*;
Cycloconium diseases, caused for example by *Cycloconium oleaginum*;
Diaporthe diseases, caused for example by *Diaporthe citri*;
Elsinoe diseases, caused for example by *Elsinoe fawcettii*;
Gloeosporium diseases, caused for example by *Gloeosporium laeticolor*;
Glomerella diseases, caused for example by *Glomerella cingulata*;
Guignardia diseases, caused for example by *Guignardia bidwelli*;
Leptosphaeria diseases, caused for example by *Leptosphaeria maculans*; *Leptosphaeria nodorum*;
Magnaporthe diseases, caused for example by *Magnaporthe grisea*;
Mycosphaerella diseases, caused for example by *Mycosphaerella graminicola*; *Mycosphaerella* arachidicola; Mycosphaerella fijiensis;
Phaeosphaeria diseases, caused for example by *Phaeosphaeria nodorum*;
Pyrenophora diseases, caused for example by *Pyrenophora teres*;
Ramularia diseases, caused for example by *Ramularia collo-cygni*;
Rhynchosporium diseases, caused for example by *Rhynchosporium secalis*;
Septoria diseases, caused for example by *Septoria apii* or *Septoria lycopercisi*;
Typhula diseases, caused for example by *Typhula incamata*;
Venturia diseases, caused for example by *Venturia inaequalis*:
Root and stem diseases such as:
Corticium diseases, caused for example by *Corticium graminearum*;
Fusarium diseases, caused for example by *Fusarium oxysporum*;
Gaeumannomyces diseases, caused for example by *Gaeumannomyces graminls*;
Rhizoctonia diseases, caused for example by *Rhizoctonia solani*;
Tapesia diseases, caused for example by *Tapesia acuformis*;
Thielaviopsis diseases, caused for example by *Thielaviopsis basicola*;
Ear and panicle diseases such as:
Alternaria diseases, caused for example by *Alternaria* spp.
Aspergillus diseases, caused for example by *Aspergillus flavus*;
Cladosporium diseases, caused for example by *Cladosporium* spp.
Claviceps diseases, caused for example by *Claviceps purpurea*;
Fusarium diseases, caused for example by *Fusarium culmorum*;
Gibberella diseases, caused for example by *Gibberella zeae*;
Monographella diseases, caused for example by *Monographella nivalis*;
Smut and bunt diseases such as:
Sphacelotheca diseases, caused for example by *Sphacelotheca reiliana*;
Tilletia diseases, caused for example by *Tilletia caries*;
Urocystis diseases, caused for example by *Urocystis occulta*;
Ustilago diseases, caused for example by *Ustilago nuda*;
Fruit rot and mould diseases such as:
Aspergillus diseases, caused for example by *Aspergillus flavus*;
Botrytis diseases, caused for example by *Botrytis cinerea*;
Penicillium diseases, caused for example by *Penicillium expansum*;
Sclerotinia diseases, caused for example by *Sclerotinia sclerotiorum*;

*Verticilium* diseases, caused for example by *Verticillum alboatrum;*

Seed and soilborne decay, mould, wilt, rot and damping-off diseases:
*Fusarium* diseases, caused for example by *Fusarium culmorum;*
*Phytophthora* diseases, caused for example by *Phytophthora cactorum;*
*Pythium* diseases, caused for example by *Pythium ultimum;*
*Rhizoctonia* diseases, caused for example by *Rhizoctonia solani;*
*Scierotium* diseases, caused for example by *Scierotium rolfsii;*
*Microdochium* diseases, caused for example by *Microdochium nivale;*

Canker, broom and dieback diseases such as:
*Nectria* diseases, caused for example by *Nectria galligena;*

Blight diseases such as:
*Monilinia* diseases, caused for example by *Monilinia laxa;*

Leaf blister or leaf curl diseases such as:
*Taphrina* diseases, caused for example by *Taphrina deformans;*

Decline diseases of wooden plants such as:
*Esca* diseases, caused for example by *Phaemoniella clamydospora;*
*Eutypa* dyeback, caused for example by *Eutypa lata;*
Dutch elm disease, caused for example by *Ceratocystsc ulmi;*

Diseases of flowers and Seeds such as:
*Botrytis* diseases, caused for example by *Botrytis cinerea;*

Diseases of tubers such as:
*Rhizoctonia* diseases, caused for example by *Rhizoctonia solani.*

Among the damaging pests or insects that can be controlled at any development stage according to the insecticide method of the invention, mention may be made to:

the order of the Anoplura (Phthiraptera), for example, *Damalinia* spp., *Haematopinus* spp., *Linognathus* spp., *Pediculus* spp., *Trichodectes* spp.;

the class of the Arachnida, for example, *Acarus siro, Aceria sheldoni, Aculops* spp., *Aculus* spp., *Amblyomma* spp., *Argas* spp., *Boophilus* spp., *Brevipalpus* spp., *Bryobia praetiosa, Chorioptes* spp., *Dermanyssus gallinae, Eotetranychus* spp., *Epitrimerus pyri, Eutetranychus* spp., *Eriophyes* spp., *Hemitarsonemus* spp., *Hyalomma* spp., *Ixodes* spp., *Latrodectus mactans, Metatetranychus* spp., *Oligonychus* spp., *Ornithodoros* spp., *Panonychus* spp., *Phyllocoptruta oleivora, Polyphagotarsonemus latus, Psoroptes* spp., *Rhipicephalus* spp., *Rhizoglyphus* spp., *Sarcoptes* spp., *Scorpio maurus, Stenotarsonemus* spp., *Tarsonemus* spp., *Tetranychus* spp., *Vasates lycopersici;* the class of the Bivalve, for example, *Dreissena* spp.;

the order of the Chilopoda, for example, *Geophilus* spp., *Scutigera* spp.;

the order of the Coleoptera, for example, *Acanthoscelides obtectus, Adoretus* spp., *Agelastica alni, Agriotes* spp., *Amphimallon solstitialis, Anobium punctatum, Anoplophora* spp., *Anthonomus* spp., *Anthrenus* spp., *Apogonia* spp., *Atomatia* spp., *Attagenus* spp., *Bruchidius obtectus, Bruchus* spp., *Ceuthorhynchus* spp., *Cleonus mendicus, Conoderus* spp., *Cosmopolites* spp., *Costelytra zealandica, Curcullo* spp., *Cryptorhynchus lapathi, Dermestes* spp., *Diabrotica* spp., *Epilachna* spp., *Faustinus cubae, Gibbium psylloides, Heteronychus arator, Hylamorpha elegans, Hylotrupes bajulus, Hypera postica, Hypothenemus* spp., *Lachnostema consanguinea, Leptinotarsa decemlineata, Lissorhoptrus oryzophilus, Lixus* spp., *Lyctus* spp., *Meligethes aeneus, Melolontha melolontha, Migdolus* spp., *Monochamus* spp., *Naupactus xanthographus, Niptus hololeucus, Oryctes rhinoceros, Oryzaephilus surinamensis, Otiorrhynchus sulcatus, Oxycetonia jucunda, Phaedon cochleariae, Phyllophaga* spp., *Popillia japonica, Premnotrypes* spp., *Psylliodes chrysocephala, Ptinus* spp., *Rhizobius ventralis, Rhizopertha dominica, Sitophilus* spp., *Sphenophorus* spp., *Stemechus* spp., *Symphyletes* spp., *Tenebrio molitor, Tribolium* spp., *Trogoderma* spp., *Tychius* spp., *Xylotrechus* spp., *Zabrus* spp.

the order of the Collembola, for example, *Onychiurus armatus;* the order of the Dermaptera, for example, *Forficula auricularia;* the order of the Diplopoda, for example, *Blaniulus guttulatus;* the order of the Diptera, for example, *Aedes* spp., *Anopheles* spp., *Bibio hortulanus, Calliphora erythrocephala, Ceratitis capitata, Chrysomyia* spp., *Cochliomyia* spp., *Cordylobia anthropophaga, Culex* spp., *Cuterebra* spp., *Dacus oleae, Dermatobia hominis, Drosophila* spp., *Fannia* spp., *Gastrophilus* spp., *Hylemyia* spp., *Hyppobosca* spp., *Hypoderma* spp., *Liriomyza* spp., *Lucilia* spp., *Musca* spp., *Nezara* spp., *Oestrus* spp., *Oscinella frit, Pegomyia hyoscyami, Phorbia* spp., *Stomoxys* spp., *Tabanus* spp., *Tannia* spp., *Tipula paludosa, Wohlfahrtia* spp;

the class of the Gastropoda, for example, *Arion* spp., *Biomphalaria* spp., *Bulinus* spp., *Deroceras* spp., *Galba* spp., *Lymnaea* spp., *Oncomelania* spp., *Succinea* spp.;

the class of the helminths, for example, *Ancylostoma duodenale, Ancylostoma ceylanicum, Acylostoma braziliensis, Ancylostoma* spp., *Ascaris lubricoides, Ascaris* spp., *Brugia malayi, Brugia timori, Bunostomum* spp., *Chabertia* spp., *Clonorchis* spp., *Cooperia* spp., *Dicrocoelium* spp, *Dictyocaulus frlaria, Diphyllobothrium latum, Dracunculus medinensis, Echinococcus granulosus, Echinococcus multilocularis, Enterobius vermicularis, Faciola* spp., *Haemonchus* spp., *Heterakis* spp., *Hymenolepis nana, Hyostrongulus* spp., *Loa Loa, Nematodirus* spp., *Oesophagostomum* spp., *Opisthorchis* spp., *Onchocerca volvulus, Ostertagia* spp., *Paragonimus* spp., *Schistosomen* spp, *Strongyloides fuellebomi, Strongyloides stercoralis, Stronyloides* spp., *Taenia saginata, Taenia solium, Trichinella spiralis, Trichinella nativa, Trichinella* britovi, *Trichinella nelsoni, Trichinella pseudopsiralis, Trichostrongulus* spp., *Trichuris* trichuria, *Wuchereria bancrofti;*

Protozoa, such as *Eimeria;* the order of the Heteroptera, for example, *Anasa tristis, Antestiopsis* spp., *Blissus* spp., *Calocoris* spp., *Campylomma livida, Cavelerius* spp., *Cimex* spp., *Creontiades dilutus, Dasynus piperis, Dichelops furcatus, Diconocoris hewetti, Dysdercus* spp., *Euschistus* spp., *Eurygaster* spp., *Heliopeltis* spp., *Horcias nobilellus, Leptocorisa* spp., *Leptoglossus phyllopus, Lygus* spp., *Macropes excavatus, Miridae, Nezara* spp., *Oebalus* spp., *Pentomidae, Piesma quadrata, Piezodorus* spp., *Psallus seriatus, Pseudacysta persea, Rhodnius* spp., *Sahlbergella singularis, Scotinophora* spp., *Stephanitis nashi, Tibraca* spp., *Triatoma* spp;

the order of the Homoptera, for example, *Acyrthosipon* spp., *Aeneolamia* spp., *Agonoscena* spp., *Aleurodes* spp.,

*Aleurolobus barodensis, Aleurothrixus* spp., *Amrasca* spp., *Anuraphis cardui, Aonidiella* spp., *Aphanostigma piri, Aphis* spp., *Arboridia apicalis, Aspidiella* spp., *Aspidiotus* spp., *Atanus* spp., *Aulacorthum solani, Bemisia* spp., *Brachycaudus helichrysii, Brachycolus* spp., *Brevicoryne brassicae, Calligypona marginata, Cameocephala fulgida, Ceratovacuna lanigera, Cercopidae, Ceroplastes* spp., *Chaetosiphon fragaefolil, Chionaspis tegalensis, Chlorita onukii, Chromaphis juglandicola, Chrysomphalus ficus, Cicadulina mbila, Coccomytilus halli, Coccus* spp., *Cryptomyzus ribis, Dalbulus* spp., *Dialeurodes* spp., *Diaphorina* spp., *Diaspis* spp., *Doralis* spp., *Drosicha* spp., *Dysaphis* spp., *Dysmicoccus* spp., *Empoasca* spp., *Enosoma* spp., *Erythroneura* spp., *Euscelis bilobatus, Geococcus coffeae, Homalodisca coagulata, Hyalopterus arundinis, Icerya* spp., *Idiocerus* spp., *Idioscopus* spp., *Laodelphax striatellus, Lecanium* spp., *Lepidosaphes* spp., *Lipaphis erysimi, Macrosiphum* spp., *Mahanarva flmbriolata, Melanaphis sacchari, Metcalflella* spp., *Metopolophium dirhodum, Monellia costalis, Monelliopsis pecanis, Myzus* spp., *Nasonovia ribisnigri, Nephotettix* spp., *Nilaparvata lugens, Oncometopia* spp., *Orthezia praelonga, Parabemisia myricae, Paratrioza* spp., *Parlatoria* spp., *Pemphigus* spp., *Peregrinus maidis, Phenacoccus* spp., *Phloeomyzus passerini, Phorodon humuli, Phylloxera* spp., *Pinnaspis aspidistrae, Planococcus* spp., *Protopulvinaria pyriformis, Pseudaulacaspis pentagona, Pseudococcus* spp., *Psylla* spp., *Pteromalus* spp., *Pyrila* spp., *Quadraspidiotus* spp., *Quesada gigas, Rastrococcus* spp., *Rhopalosiphum* spp., *Saissetia* spp., *Scaphoides titanus, Schizaphis graminum, Selenaspidus articulatus, Sogata* spp., *Sogatella furcifera, Sogatodes* spp., *Stictocephala festina, Tenalaphara malayensis, Tinocallis caryaefoliae, Tomaspis* spp., *Toxoptera* spp., *Trialeurodes vaporariorum, Trioza* spp., *Typhlocyba* spp., *Unaspis* spp., *Viteus vitifolii;* the order of the Hymenoptera, for example, *Diprion* spp., *Hoplocampa* spp., *Lasius* spp., *Monomorium pharaonis, Vespa* spp.;

the order of the Isopoda, for example, *Armadillidium vulgare, Oniscus asellus, Porcellio scaber;* the order of the Isoptera, for example, *Reticulitermes* spp., *Odontotermes* spp.;

the order of the Lepidoptera, for example, *Acronicta major, Aedia leucomelas, Agrotis* spp., *Alabama argillacea, Anticarsia* spp., *Barathra brassicae, Bucculatrix thurberiella, Bupalus piniarius, Cacoecia podana, Capua reticulana, Carpocapsa pomonella, Chematobia brumata, Chilo* spp., *Choristoneura fumiferana, Clysia ambiguella, Cnaphalocerus* spp., *Earias insulana, Ephestia kuehniella, Euproctis chrysorrhoea, Euxoa* spp., *Feltia* spp., *Galleria mellonella, Helicoverpa* spp., *Heliothis* spp., *Hofmannophila pseudospretella, Homona magnanima, Hyponomeuta padella, Laphygma* spp., *Lithocolletis blancardella, Lithophane antennata, Loxagrotis albicosta, Lymantria* spp., *Malacosoma neustria, Mamestra brassicae, Mocis repanda, Mythimna separata, Oria* spp., *Oulema oryzae, Panolls flammea, Pectinophora gossypiella, Phyllocnistis citrella, Pieris* spp., *Plutella xylostella, Prodenia* spp., *Pseudaletia* spp., *Pseudoplusia includens, Pyrausta nubilalis, Spodoptera* spp., *Thermesia gemmatalis, Tinea pellionella, Tineola bisselliella, Toffrix vimidana, Trichoplusia* spp.;

the order of the Orthoptera, for example, *Acheta domesticus, Blafta orientalis, Blattella germanica, Gryllotalpa* spp., *Leucophaea maderae, Locusta* spp., *Melanoplus* spp., *Periplaneta americana, Schistocerca gregaria;* the order of the Siphonaptera, for example, *Ceratophyllus* spp., *Xenopsylla cheopis.* the order of the Symphyla, for example, *Scutigerella immaculate;* the order of the Thysanoptera, for example, *Baliothrips biformis, Enneothrips flavens, Frankliniella* spp., *Heliothrips* spp., *Hercinothrips femoralis, Kakothrips* spp., *Rhipiphorothrips cruentatus, Scirtothrips* spp., *Taeniothrips cardamoni, Thrips* spp.;

the order of the Thysanura, for example, *Lepisma saccharina;* the phytoparasitic nematodes including for example, *Anguina* spp., *Aphelenchoides* spp., *Belonoaimus* spp., *Bursaphelenchus* spp., *Ditylenchus dipsaci, Globodera* spp., *Heliocotylenchus* spp., *Heterodera* spp., *Longidorus* spp., *Meloidogyne* spp., *Pratylenchus* spp., *Radopholus similis, Rotylenchus* spp., *Trichodorus* spp., *Tylenchorhynchus* spp., *Tylenchulus* spp., *Tylenchulus semipenetrans, Xiphinema* spp;

the beetles, such as *Hylotrupes bajulus, Chlorophorus pilosis, Anobium punctatum, Xestobium rufovillosum, Ptilinus pecticornis, Dendrobium peffinex, Ernobius mollis, Priobium carpini, Lyctus brunneus, Lyctus africanus, Lyctus planicollis, Lyctus linearis, Lyctus pubescens, Trogoxylon aequale, Minthes rugicollis, Xyleborus* spec. *Tryptodendron* spec. *Apate monachus, Bostrychus capucins, Heterobostrychus brunneus, Sinoxylon* spec. *Dinoderus minutus;*

Hymenopterons, such as *Sirex juvencus, Urocerus gigas, Urocerus gigas taignus, Urocerus augur;* termites, such as *Kalotermes flavicollis, Cryptotermes brevis, Heterotermes indicola, Reticulitermes flavipes, Reticulitermes santonensis, Reticulitermes lucifugus, Mastotermes darwiniensis, Zooternopsis nevadensis, Coptotermes formosanus;*

Bristletails, such as *Lepisma saccharina;* the order of the Acarina, for example, *Argas persicus, Argas reflexus, Bryobia* ssp., *Dermanyssus gallinae, Glyciphagus domesticus, Ornithodorus moubat, Rhipicephalus sanguineus, Trombicula alfreddugesi, Neutrombicula autumnalis, Dermatophagoides pteronissimus, Dermatophagoides forinae;* the order of the Araneae, for example, Aviculariidae, Araneidae;

the order of the Opiliones, for example, *Pseudoscorpiones chelifer, Pseudoscorpiones cheiridium, Opiliones phalangium;* the order of the Isopoda, for example, *Oniscus asellus, Porcellio scaber;* the order of the Diplopoda, for example, *Blaniulus guttulatus, Polydesmus* spp.;

the order of the Chilopoda, for example, *Geophilus* spp.;

the order of the Zygentoma, for example, *Ctenolepisma* spp., *Lepisma saccharina, Lepismodes inquilinus;* the order of the Blattaria, for example, *Blatta orientalies, Blattella germanica, Blattella asahinal, Leucophaea maderae, Panchlora* spp., *Parcoblafta* spp., *Periplaneta australasiae, Periplaneta americana, Periplaneta brunnea, Periplaneta fuliginosa, Supella longipalpa;* the order of the Saltatoria, for example, *Acheta domesticus;* the order of the Dernaptera, for example, *Fofficula auricularia;* the order of the Isoptera, for example, *Kalotermes* spp., *Reticulltermes* spp;

the order of the Psocoptera, for example, *Lepinatus* spp., *Liposcelis* spp;

the order of the Coleoptera, for example, *Anthrenus* spp., *Attagenus* spp., *Dermestes* spp.; *Latheticus oryzae, Necrobia* spp., *Ptinus* spp., *Rhizopeftha dominica, Sitophilus granarius, Sitophilus oryzae, Sitophilus zeamais, Stegobium paniceum.* the order of the Diptera, for example, *Aedes aegypti, Aedes albopictus, Aedes taeniorhynchus, Anopheles* spp., *Calliphora erythrocephala, Chrysozona pluvialis, Culex quinquefasciatus, Culex pipiens, Culex tarsalis, Drosophila* spp., *Fannia canicularis, Musca domestica, Phlebotomus* spp., *Sarcophaga camaria, Simulium* spp., *Stomoxys calcitrans, Tipula paludosa;* the order of the Lepidoptera, for example, *Achroia grisella, Galleria mellonella, Plodia interpunctella, Tinea cloacella, Tinea pellionella, Tineola bisselliella;* the order of the Siphonaptera, for example, *Ctenocephalides canis, Ctenocephalides felis, Pulex irritans, Tunga penetrans, Xenopsylla cheopis.* the order of the Hymenoptera, for example, *Camponotus herculeanus, Lasius fuliginosus, Lasius niger, Lasius umbratus, Monomorium pharaonis, Paravespula* spp., *Tetramorium caespitum;* the order of the Anoplura, for example, *Pediculus humanus capitis, Pediculus humanus corporis, Pemphigus* spp., *Phylloera vastatrix, Phthirus pubis;* the order of the Heteroptera, for example, *Cimex hemipterus, Cimex lectularius, Rhodinus prolixus, Triatoma infestans.*

The fungicide or insecticide composition according to the invention may also be used against fungal diseases or damaging insects liable to grow or attack on or inside timber. The term "timber" means all types of species of wood, and all types of working of this wood intended for construction, for example solid wood, high-density wood, laminated wood, and plywood. The method for treating timber according to the invention mainly consists in contacting one or more compounds according to the invention, or a composition according to the invention; this includes for example direct application, spraying, dipping, injection or any other suitable means.

The dose of active compound usually applied in the method of treatment according to the invention is generally and advantageously from 10 to 800 g/ha, preferably from 50 to 300 g/ha for applications in foliar treatment. The dose of active substance applied is generally and advantageously from 2 to 200 g per 100 kg of seed, preferably from 3 to 150 g per 100 kg of seed in the case of seed treatment.

It is clearly understood that the doses indicated herein are given as illustrative examples of the method according to the invention. A person skilled in the art will know how to adapt the application doses, notably according to the nature of the plant or crop to be treated.

The fungicide or insecticide composition according to the invention may also be used in the treatment of genetically modified organisms with the compounds according to the invention or the agrochemical compositions according to the invention. Genetically modified plants are plants into genome of which a heterologous gene encoding a protein of interest has been stably integrated. The expression "heterologous gene encoding a protein of interest" essentially means genes which give the transformed plant new agronomic properties, or genes for improving the agronomic quality of the modified plant.

The compounds or mixtures according to the invention may also be used for the preparation of composition useful to curatively or preventively treat human or animal fungal diseases such as, for example, mycoses, dermatoses, *trichophyton* diseases and candidiases or diseases caused by *Aspergillus* spp., for example *Aspergillus fumigatus.*

The various aspects of the invention will now be illustrated with reference to the following tables of compounds examples. The following tables illustrate in a non-limiting manner examples of compounds according to the invention.

In the following examples, M+1 (or M−1) means the molecular ion peak, plus or minus 1 a.m.u. (atomic mass unit) respectively, as observed in mass spectroscopy and M (Apcl+) means the molecular ion peak as it was found via positive atmospheric pressure chemical ionisation in mass spectroscopy.

In the following examples, the logP values were determined in accordance with EEC Directive 79/831 Annex V.A8 by HPLC (High Performance Liquid Chromatography) on a reversed-phase column (C 18), using the method described below:

Temperature: 40° C.; Mobile phases: 0.1% aqueous formic acid and acetonitrile; linear gradient from 10% acetonitrile to 90% acetonitrile.

Calibration was carried out using unbranched alkan-2-ones (comprising 3 to 16 carbon atoms) with known logP values (determination of the logP values by the retention times using linear interpolation between two successive alkanones).

The lambda max values were determined in the maxima of the chromatographic signals using the UV spectra from 190 nm to 400 nm.

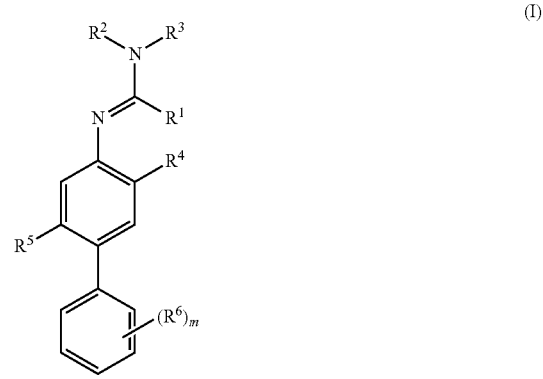

(I)

TABLE 1

| No. | R1 | R2 | R3 | R1 | R4 | R5 | R6 ortho | R6 meta | R6 para | meta¹ | log p (HCOOH) |
|---|---|---|---|---|---|---|---|---|---|---|---|
| 1 | H | Me | Et | H | Cl | H | H | H | tBu | H | 2.44 |
| 2 | H | Me | Et | H | CF3 | H | H | H | tBu | H | 2.83 |
| 3 | H | Me | Et | H | Cl | H | H | Cl | F | H | 1.92 |
| 4 | H | Me | Et | H | CF3 | H | H | Cl | F | H | 2.36 |
| 5 | H | Me | Et | H | Me | H | H | Cl | F | H | 2.00 |

TABLE 1-continued

| No. | R1 | R2 | R3 | R1 | R4 | R5 | R6 ortho | R6 meta | R6 para | R6 meta[1] | log p (HCOOH) |
|---|---|---|---|---|---|---|---|---|---|---|---|
| 6 | H | Me | Et | H | F | H | H | H | tBu | H | 2.29 |
| 7 | H | Me | Et | H | Et | H | H | H | tBu | H | 2.66 |
| 8 | H | Me | Et | H | Me | Me | H | H | tBu | H | 2.67 |
| 9 | H | Me | Et | H | F | H | H | Cl | F | H | 1.78 |
| 10 | H | Me | Et | H | Et | H | H | Cl | F | H | 2.17 |
| 11 | H | Me | Et | H | CF3 | H | OMe | OMe | OMe | H | 1.84 |
| 12 | H | Me | Et | H | F | H | OMe | OMe | OMe | H | 1.50 |
| 13 | H | Me | Et | H | Cl | H | H | H | F | H | 1.69 |
| 14 | H | Me | Et | H | CF3 | H | H | H | F | H | 1.93 |
| 15 | H | Me | Et | H | F | H | H | H | F | H | 1.50 |
| 16 | H | Me | Et | H | Me | H | H | CF3 | Cl | H | 2.28 |
| 17 | H | Me | Et | H | Me | Me | H | CF3 | Cl | H | 2.40 |
| 18 | H | Me | Et | H | Cl | H | H | CF3 | Cl | H | 2.19 |
| 19 | H | Me | Et | H | CF3 | H | H | CF3 | Cl | H | 2.90 |
| 20 | H | Me | Et | H | F | H | H | CF3 | Cl | H | 2.15 |
| 21 | H | Me | Et | H | Et | H | H | CF3 | Cl | H | 2.39 |
| 22 | H | Me | Et | H | Me | Me | H | H | F | H | 1.95 |
| 23 | H | Me | Et | H | Et | H | H | H | F | H | 1.79 |
| 24 | H | Me | Et | H | Cl | H | H | H | CF3 | H | 1.99 |
| 25 | H | Me | Et | H | CF3 | H | H | H | CF3 | H | 2.54 |
| 26 | H | Me | Et | H | F | H | H | H | CF3 | H | 1.87 |
| 27 | H | Me | Et | H | Et | H | H | H | CF3 | H | 2.20 |
| 28 | SH | Me | Et | SH | Me | Me | H | H | tBu | H | 4.58 |
| 29 | H | Me | Et | H | Me | H | H | OMe | OMe | OMe | 1.56 |
| 30 | H | Me | Et | H | Me | H | H | H | C=NOMe | H | 1.94 |
| 31 | H | Me | Et | H | Me | H | H | H | CMe=NOMe | H | 2.02 |
| 32 | H | Me | Et | H | Me | H | H | Cl | Cl | H | 2.21 |
| 33 | H | Me | Et | H | Me | H | H | Me | F | H | 2.04 |
| 34 | H | Me | Et | H | Me | H | H | F | F | H | 1.89 |
| 35 | H | Me | Et | H | Me | H | H | H | OPh | H | 2.41 |
| 36 | H | Me | Et | H | Me | H | H | H | OCH2Ph | H | 2.46 |
| 37 | H | Me | Et | H | Me | H | H | H | CH2OMe | H | 1.59 |
| 38 | H | Me | Et | H | Me | H | H | OMe | OMe | H | 1.49 |
| 39 | H | Me | Et | H | Me | Me | H | OMe | OMe | OMe | 1.68 |
| 40 | H | Me | Et | H | Me | Me | H | H | C=NOMe | H | 2.05 |
| 41 | H | Me | Et | H | Me | Me | H | F | Cl | H | 2.32 |
| 42 | H | Me | Et | H | Me | Me | H | H | CMe=NOMe | H | 2.24 |
| 43 | H | Me | Et | H | Me | Me | F | F | F | H | 2.32 |
| 44 | H | Me | Et | H | Me | Me | H | Cl | Cl | H | 2.27 |
| 45 | H | Me | Et | H | Me | Me | H | Me | F | H | 2.08 |
| 46 | H | Me | Et | H | Me | Me | H | F | F | H | 1.98 |
| 47 | H | Me | Et | H | Me | Me | H | H | OPh | H | 2.56 |
| 48 | H | Me | Et | H | Me | Me | H | H | OCH2Ph | H | 2.55 |
| 49 | H | Me | Et | H | Me | Me | H | H | CH2OMe | H | 1.76 |
| 50 | H | Me | Et | H | Et | H | H | OMe | OMe | OMe | 1.69 |
| 51 | H | Me | Et | H | Et | H | H | H | C=NOMe | H | 2.09 |
| 52 | H | Me | Et | H | Et | H | H | F | Cl | H | 2.31 |
| 53 | H | Me | Et | H | Et | H | H | H | CMe=NOMe | H | 2.19 |
| 54 | H | Me | Et | H | Et | H | H | Cl | Cl | H | 2.37 |
| 55 | H | Me | Et | H | Et | H | H | Me | F | H | 1.98 |
| 56 | H | Me | Et | H | Et | H | H | F | F | H | 2.00 |
| 57 | H | Me | Et | H | Et | H | Cl | H | Cl | H | 2.26 |
| 58 | H | Me | Et | H | Et | H | H | H | OMe | H | 1.90 |
| 59 | H | Me | Et | H | Et | H | H | H | OPh | H | 2.32 |
| 60 | H | Me | Et | H | Et | H | H | H | OCH2Ph | H | 2.39 |
| 61 | H | Me | Et | H | Et | H | H | H | CH2OMe | H | 1.67 |
| 62 | H | Me | Et | H | Et | H | H | OMe | OMe | H | 1.68 |
| 63 | H | Me | Et | H | Cl | H | H | OMe | OMe | OMe | 1.58 |
| 64 | H | Me | Et | H | Cl | H | H | H | C=NOMe | H | 1.87 |
| 65 | H | Me | Et | H | Cl | H | H | H | CMe=NOMe | H | 2.00 |
| 66 | H | Me | Et | H | Cl | H | H | Cl | Cl | H | 2.25 |
| 67 | H | Me | Et | H | Cl | H | H | Me | F | H | 2.10 |
| 68 | H | Me | Et | H | Cl | H | H | F | F | H | 1.83 |
| 69 | H | Me | Et | H | Cl | H | Cl | H | Cl | H | 2.32 |
| 70 | H | Me | Et | H | Cl | H | H | H | OMe | H | 1.71 |
| 71 | H | Me | Et | H | Cl | H | H | H | OPh | H | 2.45 |
| 72 | H | Me | Et | H | Cl | H | H | H | OCH2Ph | H | 2.48 |
| 73 | H | Me | Et | H | Cl | H | H | H | CH2OMe | H | 1.65 |
| 74 | H | Me | Et | H | Cl | H | H | OMe | OMe | H | 1.54 |
| 75 | H | Me | Et | H | CF3 | H | H | OMe | OMe | OMe | 1.79 |
| 76 | H | Me | Et | H | CF3 | H | H | H | C=NOMe | H | 2.01 |
| 77 | H | Me | Et | H | F | H | H | H | C=NOMe | H | 1.73 |
| 78 | H | Me | Et | H | CF3 | H | H | H | CMe=NOMe | H | 2.24 |
| 79 | H | Me | Et | H | CF3 | H | F | F | F | H | 2.29 |
| 80 | H | Me | Et | H | CF3 | H | H | H | Br | H | 2.24 |
| 81 | H | Me | Et | H | CF3 | H | H | Cl | Cl | H | 2.57 |

TABLE 1-continued

| No. | R1 | R2 | R3 | R1 | R4 | R5 | R6 ortho | R6 meta | R6 para | R6 meta[1] | log p (HCOOH) |
|---|---|---|---|---|---|---|---|---|---|---|---|
| 82 | H | Me | Et | H | CF3 | H | H | Me | F | H | 2.20 |
| 83 | H | Me | Et | H | CF3 | H | H | F | F | H | 2.09 |
| 84 | H | Me | Et | H | F | H | H | F | F | H | 1.68 |
| 85 | H | Me | Et | H | CF3 | H | Cl | H | Cl | H | 2.39 |
| 86 | H | Me | Et | H | F | H | Cl | H | Cl | H | 2.05 |
| 87 | H | Me | Et | H | CF3 | H | H | H | OMe | H | 1.78 |
| 88 | H | Me | Et | H | F | H | H | H | OMe | H | 1.59 |
| 89 | H | Me | Et | H | CF3 | H | H | H | OPh | H | 2.65 |
| 90 | H | Me | Et | H | F | H | H | H | OPh | H | 2.20 |
| 91 | H | Me | Et | H | CF3 | H | H | H | OCH2Ph | H | 2.43 |
| 92 | H | Me | Et | H | F | H | H | H | OCH2Ph | H | 2.27 |
| 93 | H | Me | Et | H | CF3 | H | H | H | CH2OMe | H | 1.76 |
| 94 | H | Me | Et | H | CF3 | H | H | OMe | OMe | H | 1.71 |
| 95 | H | Me | Et | H | F | H | H | OMe | OMe | H | 1.41 |
| 96 | H | Me | Et | H | H | Cl | H | Cl | H | H | 1.92 |
| 97 | H | Me | Et | H | OMe | OMe | H | Cl | OMe | H | 1.83 |
| 98 | H | Me | Et | H | OMe | OMe | H | H | Me | H | 1.89 |
| 99 | H | Me | Et | H | Me | F | H | H | Cl | H | 2.23 |
| 100 | H | Me | Et | H | H | Cl | H | H | OCF3 | H | 2.15 |
| 101 | H | Me | iPr | H | H | Cl | H | Cl | H | H | 2.04 |
| 102 | H | Me | iPr | H | OMe | OMe | H | Cl | OMe | H | 1.95 |
| 103 | H | Me | iPr | H | OMe | OMe | H | H | Me | H | 2.01 |
| 104 | H | Me | iPr | H | Me | F | H | H | Cl | H | 2.22 |
| 105 | H | Me | iPr | H | H | Cl | H | H | OCF3 | H | 2.42 |
| 106 | H | Me | Et | H | Cl | Me | H | H | tBu | H | 2.71 |
| 107 | H | Me | Et | H | Cl | Me | H | CF3 | Cl | H | 2.30 |
| 108 | H | Me | Et | H | Me | H | H | Me | Cl | H | 2.14 |
| 109 | H | Me | Et | H | Me | Me | H | Me | Cl | H | 2.27 |
| 110 | H | Me | Et | H | Cl | H | H | Me | Cl | H | 2.13 |
| 111 | H | Me | Et | H | Me | H | Me | H | Cl | H | 2.23 |
| 112 | H | Me | Et | H | Me | Me | Me | H | Cl | H | 2.24 |
| 113 | H | Me | Et | H | Cl | H | Me | H | Cl | H | 2.03 |
| 114 | H | Me | Et | H | Me | H | H | Me | OMe | H | 2.05 |
| 115 | H | Me | Et | H | Cl | H | H | Me | OMe | H | 1.86 |
| 116 | H | CH2CH2CH2CH2CH2 | | H | Me | Me | H | H | tBu | H | 2.69 |
| 117 | H | CH2CH2CH2CH(CH3) | | H | Me | Me | H | H | tBu | H | 3.02 |
| 118 | H | CH2CH2OCH2CH2 | | H | Me | Me | H | H | tBu | H | 2.53 |
| 119 | H | CH2CH2CH2CH2 | | H | Me | Me | H | H | tBu | H | 2.79 |
| 120 | CH2CH2CH2 | H | CH2CH2CH2 | | Me | Me | H | H | tBu | H | 2.53 |
| 121 | CH2CH2CH2CH2 | H | CH2CH2CH2CH2 | | Me | Me | H | H | tBu | H | 2.60 |
| 122 | NHCH2CH2CH2 | H | NHCH2CH2CH2 | | Me | Me | H | H | Cl | H | 2.08 |
| 123 | NHCH2CH2CH2 | H | NHCH2CH2CH2 | | Me | Me | H | H | F | H | 1.81 |
| 124 | NHCH2CH2 | H | NHCH2CH2 | | Me | Me | H | H | F | H | 1.72 |
| 125 | H | Me | Et | H | Me | Me | H | H | Cl | H | 2.18 |
| 126 | H | Me | Et | H | Me | H | H | H | F | H | 1.84 |
| 127 | H | Me | Et | H | Me | H | H | H | CF3 | H | 2.17 |
| 128 | H | Me | Et | H | Me | H | H | Cl | H | H | 2.01 |
| 129 | H | Me | Et | H | Me | H | H | H | tBu | H | 2.67 |
| 130 | H | Me | Et | H | Me | H | H | H | CN | H | 1.54 |
| 131 | H | Me | Et | H | Me | Me | H | H | Me | H | 2.01 |
| 132 | H | Me | Et | H | Me | Me | H | H | CF3 | H | 2.19 |
| 133 | H | Me | Et | H | Me | Me | H | Cl | H | H | 2.15 |
| 134 | H | Me | Et | H | Me | Me | H | H | H | H | 1.77 |
| 135 | H | Me | Et | H | Me | Me | —CH=CH—CH=CH— | | | H | 2.13 |
| 136 | H | Me | Et | H | Me | Me | H | H | CN | H | 1.54 |
| 137 | H | Me | Et | H | Me | Me | H | Cl | F | H | 2.02 |
| 138 | CH2CH2CH2CH2 | H | CH2CH2CH2CH2 | | Me | H | H | H | tBu | H | 2.45 |
| 139 | H | Me | Et | H | Me | Me | H | H | CMe=NOEt | H | 2.55 |
| 140 | H | Me | Allyl | H | Me | Me | H | H | CMe=NOEt | H | 2.60 |
| 141 | H | CH2CH2CH2CH2CH2 | | H | Me | Me | H | H | CMe=NOEt | H | 2.22 |
| 142 | H | Me | Et | H | Me | Me | H | Cl | CF3 | H | 2.59 |
| 143 | H | Me | Pr | H | Me | Me | H | Cl | CF3 | H | 2.69 |
| 144 | H | Me | Allyl | H | Me | Me | H | Cl | CF3 | H | 2.70 |
| 145 | H | CH2CH2CH2CH2CH2 | | H | Me | Me | H | Cl | CF3 | H | 2.78 |
| 146 | H | Me | Et | H | Me | Me | H | Cl | Me | H | 2.37 |
| 147 | H | Me | Pr | H | Me | Me | H | Cl | Me | H | 2.56 |
| 148 | H | Me | Allyl | H | Me | Me | H | Cl | Me | H | 2.48 |
| 149 | H | CH2CH2CH2CH2CH2 | | H | Me | Me | H | Cl | Me | H | 2.53 |
| 150 | H | CH2CH2CH2CH2 | | H | Me | Me | H | Cl | Me | H | 2.37 |
| 151 | H | Me | Et | H | Me | Me | H | H | SiMe3 | H | 2.98 |
| 152 | H | Me | Pr | H | Me | Me | H | H | SiMe3 | H | 3.10 |
| 153 | H | Me | Allyl | H | Me | Me | H | H | SiMe3 | H | 3.08 |
| 154 | H | CH2CH2CH2CH2CH2 | | H | Me | Me | H | H | SiMe3 | H | 3.16 |
| 155 | H | Me | Et | H | Me | Me | H | H | iPr | H | 2.34 |
| 156 | H | Me | Pr | H | Me | Me | H | H | iPr | H | 2.70 |
| 157 | H | Me | Allyl | H | Me | Me | H | H | iPr | H | 2.60 |

TABLE 1-continued

| No. | R1 | R2 | R3 | R1 | R4 | R5 | R6 ortho | R6 meta | R6 para | R6 meta[1] | log p (HCOOH) |
|---|---|---|---|---|---|---|---|---|---|---|---|
| 158 | H | | CH2CH2CH2CH2CH2 | H | Me | Me | H | H | iPr | H | 2.60 |
| 159 | H | Me | Et | H | Me | Me | H | H | 1-Me-1-MeO-Pr | H | 2.38 |
| 160 | H | Me | Et | H | Me | Me | H | H | OtBu | H | 2.28 |
| 161 | H | Me | iPr | H | Me | Me | H | H | tBu | H | 2.77 |
| 162 | H | Me | Et | H | Me | Me | H | H | iBu | H | 2.84 |
| 163 | H | Me | Et | H | Me | Me | H | H | sBu | H | 2.92 |
| 164 | H | Me | Et | H | Me | Me | H | Br | tBu | H | 3.13 |
| 165 | H | Me | Et | H | Me | Me | H | H | cyclohexyl | H | 3.18 |
| 166 | H | Me | Et | H | Me | Me | H | H | CH2SiMe3 | H | 3.18 |
| 167 | H | Me | Et | H | Me | Me | H | H | cyclopentyl | H | 2.94 |
| 168 | H | Me | Et | H | Me | Me | H | Cl | tBu | H | 2.85 |
| 169 | H | Me | iPr | H | Me | Me | H | F | tBu | H | 2.74 |
| 170 | H | Me | Et | H | Me | Me | H | H | OiPr | H | 2.18 |
| 171 | H | Me | Et | H | Me | Me | H | Cl | OiPr | H | 2.62 |
| 172 | H | Me | Et | H | Me | Me | H | F | OiPr | H | 2.37 |
| 173 | H | Me | Et | H | Me | Me | H | H | SO2NMe2 | H | 1.76 |
| 174 | H | Me | Et | H | Me | Me | H | H | SO2CF3 | H | 2.21 |
| 175 | H | Me | Et | H | Me | Me | H | H | Br | H | 2.20 |
| 176 | Me | Me | Et | Me | Me | Me | H | H | tBu | H | 2.77 |
| 177 | H | Me | Et | H | Me | CN | H | H | tBu | H | 2.21 |
| 178 | H | Me | Et | H | Me | Me | H | iPr | H | H | 2.42 |
| 179 | H | Me | Et | H | Me | Me | H | SiMe3 | H | H | 3.00 |

The following examples illustrate in a non-limiting manner the preparation and efficacy of the compounds of formula (I) according to the invention.

Preparation Example 1

Process (a)—Compound (IIa) to Compound (VII): 4'-tert-butyl-2,5-dimethylbiphenyl-4-amine—Intermediate (VII-1)

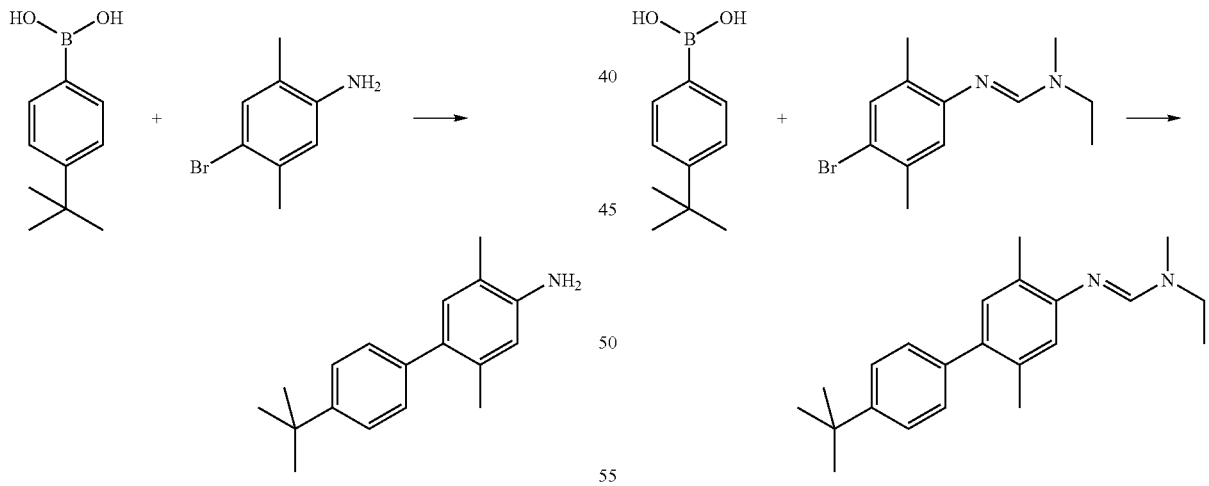

The reaction is carried out using inert conditions (argon or nitrogen atmosphere, dry solvents). A suspension of 6.4 g (36.0 mmol) of (4-tert-butylphenyl)boronic acid, 6.0 g (30.0 mmol) of 4-bromo-2,5-dimethylaniline, 29.3 g (90 mmol) caesium carbonate and 0.7 g (0.6 mmol) tetrakis(triphenylphosphin)palladium in 75 ml of 1,2-dimethoxyethan was stirred for 16 hrs at 80° C. At room temperature 25 ml of water and 75 ml of toluene were added. The organic layer was separated, the watery layer was again extracted using 75 ml of toluene. The combined organic layers were dried over magnesium sulfate and concentrated in vacuo. Column chromatographic (cyclohexane/ethylacetate:2/1) yielded 5.5 g (21.7 mmol) 72% of 4'-tert-butyl-2,5-dimethylbiphenyl-4-amine (log P (pH 2.3)=3.65.

Preparation Example 2

Process (a)—Compound (Va) to Compound (I): N'-(4'-tert-butyl-2,5-dimethylbiphenyl-4-yl)-N-ethyl-N-methylimidoformamide—Compound 8

The reaction is carried out using inert conditions (argon or nitrogen atmosphere, dry solvents). A suspension of 0.3 g (1.8 mmol) of (4-tert-butylphenyl)boronic acid, 0.4 g (1.5 mmol) of N'-(4-bromo-2,5-dimethylphenyl)-N-ethyl-N-methylimidoformamide, 1.5 g (4.5 mmol) caesium carbonate and 0.03 g (0.03 mmol) tetrakis(triphenylphosphin)palladium in 3.5 ml of 1,2-dimethoxyethan was stirred for 16 hrs at 80° C. At room temperature 5 ml of water and 15 ml of toluene were added. The organic layer was separated, the watery layer was again extracted using 15 ml of toluene. The combined organic layers were dried over magnesium sulfate and concentrated in vacuo. Column chromatographic (cyclohexane/aceton:4/1) yielded 0.23 g (0.7 mmol) 47% of N'-(4'-tert-butyl-2,5-dimethylbiphenyl-4-yl)-N-ethyl-N-methylimidoformamide; log P (pH 2.3)=2.67.

Preparation Example 3

Process (d3)—Compound (IIa) to Compound (Va): N'-(4-bromo-2,5-dimethylphenyl)-N-ethyl-N-methylimidoformamide—Intermediate (Va-1)

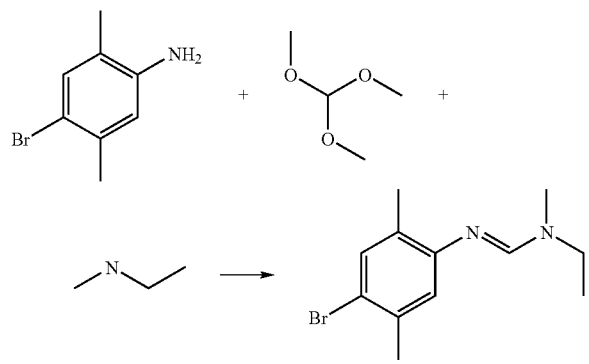

To a mixture of 10.0 g (50 mmol) of 4-bromo-2,5-dimethylaniline and 126 ml (1.15 mol) of trimethoxymethane 0.86 g (5 mmol) of p-toluene sulfonic acid were added. The reaction mixture was refluxed for 16 hrs and concentrated in vacuo. The crude product was solved in 50 ml of dichloro methane and 5.9 g (100 mmol) N-methylethanamine were added. The reaction mixture was stirred for 16 hrs at room temperature. The reaction mixture was concentrated in vacuo. Column chromatographic (gradient: petroleum ether->methyl-tert-.butyl ether) yielded 5.2 g (19.5 mmol) 39% of N'-(4-bromo-2,5-dimethylphenyl)-N-ethyl-N-methylimidoformamide; log P (pH 2.3)=1.36.

Preparation Example 4

Process (d1)—Compound (VII) to Compound (I): 4'-tert-butyl-2,5-dimethyl-N-[piperidin-2-ylidene]biphenyl-4-amine—Compound 121

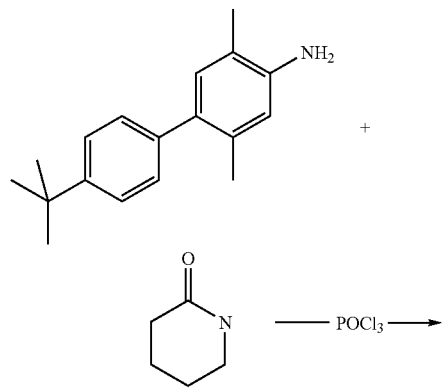

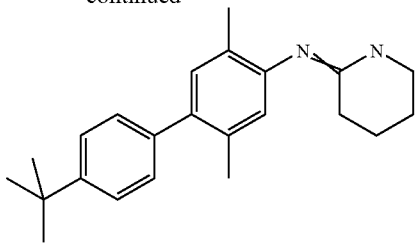

A solution of 0.2 g (1.5 mmol) of phosphoric trichloride in 5 ml toluene was added to a mixture of 0.3 g (3.0 mmol) of piperidin-2-one, the exothermic reaction was stirred for 2 hrs at ambient temperature. Then a solution of 0.38 g (1.5 mmol) of 4'-tert-butyl-2,5-dimethylbiphenyl-4-amine in 5 ml of toluene was added and the reaction mixture was refluxed for 5 hrs. At ambient temperature 5 ml of a 10% aqueous solution of sodium hydroxide was added. Separation of the layers, extraction of the watery layer with 10 ml of toluene, drying over magnesium sulfate, concentration in vacuo and column chromatographic (gradient: cyclohexane->ethyl acetate) yielded 0.3 g (1.0 mmol) 63% of 4'-tert-butyl-2,5-dimethyl-N-[piperidin-2-ylidene]biphenyl-4-amine; log P (pH 2.3)=2.6.

Preparation Example 5

Process (d2)—Compound (VII) to Compound (I): N'-(4'-tert-butyl-2,5-dimethylbiphenyl-4-yl)-N-ethyl-N-methylimidoformamide—Compound 8

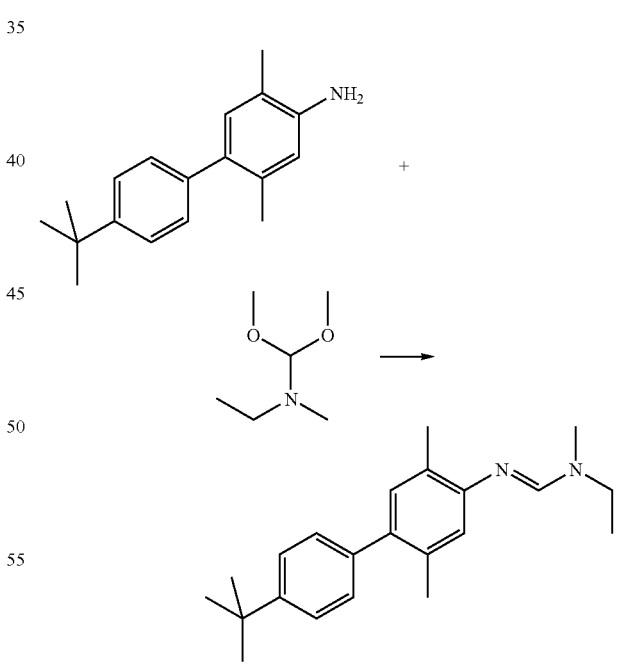

To a mixture of 2.1 g (6.3 mmol) of 4'-tert-butyl-2,5-dimethylbiphenyl-4-amine in 2.5 ml methanol a solution of 8.8 mmol of N-(dimethoxymethyl)-N-methylethanamine (60% in methanol) was added. The reaction mixture was stirred for 24 hrs at 45° C. The reaction mixture was concentrated in vacuo. Column chromatographic (gradient: cyclohexane->ethyl acetate) yielded 0.96 g (3.0 mmol) 47% of N'-(4'-tertbutyl-2,5-dimethylbiphenyl-4-yl)-N-ethyl-N-methylimido-formamide; log P (pH 2.3)=2.67.

Efficacy Example A

In Vivo Preventive Test on *Puccinia recondita* f. Sp. *tritici* (Wheat Brown Rust

| Solvent: | 50 parts by weight of n,n-dimethylacetamid |
| Emulsifier: | 1 part by weight of alkylaryl polyglycol ether |

To produce a suitable preparation of active compound, 1 part by weight of active compound is mixed with the stated amounts of solvent and emulsifier, and the concentrate is diluted with water to the desired concentration.

To test for preventive activity, young plants are inoculated with a spore suspension of *Puccinia recondita* in a 0.1% strength aqueous agar solution. After the spray coating has dried on, the plants are sprayed with the preparation of active compound at the stated rate of application. The plants remain for 24 hours in an incubation cabinet at 20° C. and a relative atmospheric humidity of 100%.

The plants are placed in a greenhouse at a temperature of approximately 20° C. and a relative atmospheric humidity of approximately 80% to promote the development of rust pustules.

The test is evaluated 10 days after the inoculation. 0% means an efficacy which corresponds to that of the control, while an efficacy of 100% means that no disease is observed.

In this test the following compounds according to the invention showed an efficacy of 70% or even higher at a concentration of 1000 ppm of active ingredient: 1, 2, 3, 7, 8, 10, 16, 17, 21, 28, 31, 33, 34, 35, 39, 4, 47, 64, 73, 96, 97, 98, 106, 107, 108, 109, 110, 112, 114, 115, 116, 122, 123, 125, 127, 129, 131, 132, 133, 136, 145, 146, 149, 151, 155, 156, 160, 162, 163, 164, 165, 167, 169.

Efficacy Example B

In Vivo Preventive Test on *Erysiphe gramini* (Powdery Mildew on Barley)

| Solvent: | 50 parts by weight of n,n-dimethylacetamid |
| Emulsifier: | 1 part by weight of alkylaryl polyglycol ether |

To produce a suitable preparation of active compound, 1 part by weight of active compound or active compound combination is mixed with the stated amounts of solvent and emulsifier, and the concentrate is diluted with water to the desired concentration.

To test for preventive activity, young plants are sprayed with the preparation of active compound or active compound combination at the stated rate of application.

After the spray coating has dried on, the plants are dusted with spores of *Erysiphe graminis* f.sp. *hordei*.

The plants are placed in a greenhouse at a temperature of approximately 20° C. and a relative atmospheric humidity of approximately 80% to promote the development of mildew pustules.

The test is evaluated 7 days after the inoculation. 0% means an efficacy which corresponds to that of the control, while an efficacy of 100% means that no disease is observed.

In this test the following compounds according to the invention showed an efficacy of 70% or even higher at a concentration of 1000 ppm of active ingredient: 1, 2, 7, 8 10, 17, 18, 21, 28, 31, 33, 34, 35, 40, 47, 73, 96, 97, 100, 106, 107, 108, 109, 112, 114, 115, 116, 123, 127, 129, 132, 133, 138.

Efficacy Example C

In Vivo Protective Test on *Alternaria solani* (Leaf Spot of Tomato)

| Solvent: | 49 parts by weight of N,N-dimethylformamide |
| Emulsifier: | 1 part by weight of alkylarylpolyglycolether |

To produce a suitable preparation of active compound, 1 part by weight of active compound is mixed with the stated amounts of solvent and emulsifier, and the concentrate is diluted with water to the desired concentration.

To test for protective activity, young plants are sprayed with the preparation of active compound at the stated rate of application. After the spray coating has dried on, the plants are inoculated with an aqueous spore suspension of *Alternaria solani*. The plants remain for one day in an incubation cabinet at approximately 20° C. and a relative atmospheric humidity of 100%. Then the plants are placed in an incubation cabinet at approximately 20° C. and a relative atmospheric humidity of 96%.

The test is evaluated 7 days after the inoculation. 0% means an efficacy which corresponds to that of the control while an efficacy of 100% means that no disease is observed.

In this test, invention related compounds of the following formula revealed an efficacy of 70% or higher at a concentration of 500 ppm of active ingredient: 8, 31, 35, 36, 39, 40, 41, 43, 47, 76, 77, 78, 106, 119, 123, 129, 132, 133.

Efficacy Example D

In Vivo Protective Test on *Podosphaera leucotricha* (Apples)

| Solvent: | 24.5 parts by weight of acetone |
| | 24.5 parts by weight of dimethylacetamide |
| Emulsifier: | 1 part by weight of alkylaryl polyglycol ether |

To produce a suitable preparation of active compound, 1 part by weight of active compound is mixed with the stated amounts of solvent and emulsifier, and the concentrate is diluted with water to the desired concentration.

To test for protective activity, young plants are sprayed with the preparation of active compound at the stated rate of application. After the spray coating has dried on, the plants are inoculated with an aqueous spore suspension of the causal agent of apple mildew (*Podosphaera leucotricha*). The plants are then placed in a greenhouse at approximately 23° C. and a relative atmospheric humidity of approximately 70%.

The test is evaluated 10 days after the inoculation. 0% means an efficacy which corresponds to that of the control, while an efficacy of 100% means that no disease is observed.

In this test the compounds according to the invention of the following structures showed efficacy of 70% or even higher at a concentration of 100 ppm of active ingredient: 1, 8, 27, 28, 40, 106, 112, 129, 132, 133, 155, 160.

Efficacy Example E

In Vivo Protective Test on *Sphaerotheca fuliginea* (Cucumbers)

| Solvent: | 24.5 parts by weight of acetone |
| --- | --- |
|  | 24.5 parts by weight of dimethylacetamide |
| Emulsifier: | 1 part by weight of alkylaryl polyglycol ether |

To produce a suitable preparation of active compound, 1 part by weight of active compound is mixed with the stated amounts of solvent and emulsifier, and the concentrate is diluted with water to the desired concentration.

To test for protect activity, young plants are sprayed with the preparation of active compound at the stated rate of application. After the spray coating has dried on, the plants are inoculated with an aqueous spore suspension of *Sphaerotheca fuliginea*. The plants are then placed in a greenhouse at approximately 23° C. and a relative atmospheric humidity of approximately 70%.

The test is evaluated 7 days after the inoculation. 0% means an efficacy which corresponds to that of the control, while an efficacy of 100% means that no disease is observed.

In this test the compounds according to the invention of the following structures showed efficacy of 70% or even higher at a concentration of 100 ppm of active ingredient: 1, 8, 17, 27, 28, 40, 106, 112, 114, 122, 123, 124, 129, 132, 133, 145, 155.

Efficacy Example F

In Vivo Protective Test on *Botrytis cinerea* (Beans)

| Solvent: | 24.5 parts by weight of acetone |
| --- | --- |
|  | 24.5 parts by weight of dimethylacetamide |
| Emulsifier: | 1 part by weight of alkylaryl polyglycol ether |

To produce a suitable preparation of active compound, 1 part by weight of active compound is mixed with the stated amounts of solvent and emulsifier, and the concentrate is diluted with water to the desired concentration.

To test for protective activity, young plants are sprayed with the preparation of active compound. After the spray coating has dried on, 2 small pieces of agar covered with growth of *Botrytis cinerea* are placed on each leaf. The inoculated plants are placed in a darkened chamber at 20° C. and a relative atmospheric humidity of 100%.

2 days after the inoculation, the size of the lesions on the leaves is evaluated. 0% means an efficacy which corresponds to that of the control, while an efficacy of 100% means that no disease is observed.

In this test the compounds according to the invention of the following structures showed efficacy of 70% or even higher at a concentration of 500 ppm of active ingredient: 8, 40, 47, 106, 129, 132, 133.

Efficacy Example G

In Vivo Protective Test on *Uromyces appendiculatus* (Beans)

| Solvent: | 24.5 parts by weight of acetone |
| --- | --- |
|  | 24.5 parts by weight of dimethylacetamide |
| Emulsifier: | 1 part by weight of alkylaryl polyglycol ether |

To produce a suitable preparation of active compound, 1 part by weight of active compound is mixed with the stated amounts of solvent and emulsifier, and the concentrate is diluted with water to the desired concentration.

To test for protective activity, young plants are sprayed with the preparation of active compound at the stated rate of application. After the spray coating has dried on, the plants are inoculated with an aqueous spore suspension of the causal agent of bean rust (*Uromyces appendiculatus*) and then remain for 1 day in an incubation cabinet at approximately 20° C. and a relative atmospheric humidity of 100%.

The plants are then placed in a greenhouse at approximately 21° C. and a relative atmospheric humidity of approximately 90%.

The test is evaluated 10 days after the inoculation. 0% means an efficacy which corresponds to that of the control, while an efficacy of 100% means that no disease is observed.

In this test the compounds according to the invention of the following structures showed efficacy of 70% or even higher at a concentration of 100 ppm of active ingredient: 129, 132, 133, 155, 160.

Efficacy Example H

In Vivo Protective Test on *Aedes Aegypti* (AEDSAEU)

| Solvent: | 1% N-methylpyrrolidone (NMP) |
| --- | --- |
|  | 1% diacetonealcohol |
| Dye: | brillantsulfoflavin for staining water |

To produce a suitable preparation of the active compound, the active compound is mixed with the stated amount of solvent, and the concentrate is diluted with staining water to the desired concentration.

*Aedes aegypti* larvae are pipetted with a preparation of active ingredient of the desired concentration.

After the specified period of time, mortality in % is determined. 100% means that all larvae have been killed, a 0% means that none of the larvae have been killed.

In this test, the following compounds from the preparation example show good activity: 9, 18, 19, 26, 47, 54, 77, 99, 100, 104, 105, 127, 128, 129.

Efficacy Example I

*Heliotis virescens*—Test on *Heliotis virescens* (HELIVI Spray Application)

| Solvent: | 78 parts by weight acetone |
| | 1.5 parts by weight dimethylformamide |
| Wetting agent | 0.5 parts by weight alkylarylpolyglcolether |

To produce a suitable preparation of the active compound, 1 part by weight of active compound is mixed with the stated amount of solvent and emulsifier, and the concentrate is dilutes with emulsifier-containing water to the desired concentration.

Soybean (*Glycine max.*) leaf sections are sprayed with a preparation of the active ingredient of the desired concentration. Once dry, the leaf sections are infested with eggs of cotton bollworm (*Heliotis virescens*).

After the specified period of time, mortality in % is determined. 100% means that all eggs have been killed and 0% means that none of the eggs have been killed.

In this test for example, the following compound from the preparation examples showed good activity: 26.

The invention claimed is:
1. A phenyl-amidine derivative of formula (I):

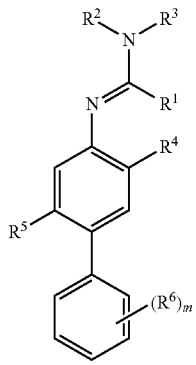

(I)

wherein
R$^1$ represents H, a substituted or non substituted C$_1$-C$_{12}$-alkyl, a substituted or non substituted C$_2$-C$_{12}$-alkenyl, a substituted or non substituted C$_2$-C$_{12}$-alkynyl, SH or a substituted or non substituted S—C$_1$-C$_{12}$-alkyl;
R$^2$ represents a substituted or non substituted C$_1$-C$_{12}$-alkyl;
R$^3$ represents a substituted or non substituted C$_2$-C$_{12}$-alkyl, substituted or non substituted C$_3$-C$_6$-cycloalkyl, substituted or non substituted C$_2$-C$_{12}$-alkenyl, substituted or non substituted C$_2$-C$_{12}$-alkynyl, halogeno-C$_1$-C$_{12}$-alkyl;
R$^1$ and R$^2$, R$^1$ and R$^3$ or R$^2$ and R$^3$ can form together a substituted or non substituted 5 to 7-membered heterocycle;

R$^4$ represents a substituted or non substituted C$_1$-C$_{12}$-alkyl, a halogen atom, halogeno-C$_1$-C$_{12}$-alkyl, substituted or non substituted O—C$_1$-C$_{12}$-alkyl or cyano;
R$^5$ represents H, a substituted or non substituted C$_1$-C$_{12}$-alkyl, a halogen atom, halogeno-C$_1$-C$_{12}$-alkyl, substituted or non substituted O—C$_1$-C$_{12}$-alkyl or cyano;
R$^6$ represents H, a halogen atom, nitro, cyano, trialkylsilyl, C$_1$-C$_8$-alkyl, substituted or non-substituted C$_1$-C$_4$-alkyl-phenyl, substituted or non-substituted phenyl, C$_1$-C$_4$-alkoxy, C$_1$-C$_4$-alkoxy-C$_1$-C$_4$-alkyl, C$_1$-C$_8$-alkylthio, C$_1$-C$_6$-halogenoalkyl, C$_1$-C$_6$-halogenalkoxy, C$_1$-C$_6$-halogenoalkylthio, substituted or non substituted C$_1$-C$_4$-alkoxy-phenyl like benzyloxy, substituted or non substituted phenoxy, substituted, non substituted alkylamino-C$_1$-C$_8$—NR$^7$R$^8$, substituted, non substituted NR$^7$R$^8$, C$_1$-C$_8$-alkyl-S(O)$_n$R$^9$, —S(O)$_n$R$^9$, C$_1$-C$_8$-alkyl-SO$_2$NR$^7$R$^8$, —SO$_2$NR$^7$R$^8$, C$_1$-C$_8$-alkyl-C(O)R$^{10}$, —CR$^9$=N—O—R$^{11}$; or
two substituents R$^6$ may form a carbocyclic or heterocyclic ring, which may comprise one or more heteroatoms selected in the list consisting of O, N, S;
n represents 0, 1 or 2;
R$^7$ and R$^8$, which may be the same or different, represent H, substituted or non-substituted C$_1$-C$_6$-alkyl;
R$^7$ and R$^8$ may form a heterocyclic ring, which may comprise one or more heteroatoms selected in the group consisting of O, N and S;
R$^9$ represents H, substituted or non-substituted, linear or branched C$_1$-C$_8$-alkyl, C$_1$-C$_8$-alkenyl, C$_1$-C$_8$-alkinyl;
R$^{10}$ represents H, substituted or non-substituted, linear or branched C$_1$-C$_8$ alkyl, C$_1$-C$_8$-alkoxy, NR$^7$R$^8$;
R$^{11}$ represents H, substituted or non-substituted, linear or branched C$_1$-C$_8$ alkyl, C$_1$-C$_4$-alkyl-phenyl, C$_1$-C$_4$-alkoxy-C$_1$-C$_4$-alkyl, substituted or non-substituted C$_1$-C$_4$-alkyl-phenyl, substituted or non-substituted phenyl;
R$^9$ and R$^{11}$ may form a heterocyclic ring, which may comprise one or more heteroatoms selected in the group consisting of O, N and S;
m represents 1, 2, 3, 4, 5.
2. A compound of formula (I) according to claim 1 wherein
R$^1$ represents H, C$_1$-C$_{12}$-alkyl or SH; or
R$^2$ represents methyl; or
R$^3$ represents C$_2$-C$_{12}$-alkyl, C$_2$-C$_{12}$-alkenyl, C$_3$-C$_6$-cycloalkyl; or
R$^2$ and R$^3$ can form together a substituted or non substituted 5 to 7-membered heterocycle; or
R$^4$ represents C$_1$-C$_{12}$-alkyl, a halogen atom or trifluoromethyl; or
R$^5$ represents H, C$_1$-C$_{12}$-alkyl, a halogen atom or trifluoromethyl; or
R$^6$ which may be the same or different, represents H; F, Cl, Br, I; nitro; cyano; C$_1$-C$_6$-alkyl; C$_1$-C$_4$-alkyl-phenyl which may be non substituted or substituted by halogen, C$_1$-C$_4$-alkyl or C$_1$-C$_4$-halogenoalkyl; phenyl which may be non substituted or substituted by halogen, C$_1$-C$_4$-alkyl or C$_1$-C$_4$-halogenoalkyl; C$_1$-C$_6$-alkoxy; C$_1$-C$_4$-alkoxy-C$_1$-C$_4$-alkyl; C$_1$-C$_6$-alkylthio; C$_1$-C$_6$-halogenoalkyl; C$_1$-C$_6$-halogenalkoxy; C$_1$-C$_6$-halogenoalkylthio; C$_1$-C$_6$-alkoxy; C$_1$-C$_4$-alkoxy-C$_1$-C$_4$-alkyl; C$_1$-C$_6$-alkylthio; benzyloxy which may be non substituted or substituted by halogen; phenoxy which may be non substituted or substituted by a halogen atom or CF$_3$; NR$^7$R$^8$; C$_1$-C$_4$-alkyl-NR$^7$R$^8$; S(O)$_n$R$^9$; C$_1$-C$_4$-alkyl-S(O)$_n$R$^9$; OR$^{10}$; C$_1$-C$_4$-alkyl-COR$^{10}$; —CR$^9$=N—O—R$^{11}$; or two substituents R⁶ may form a carbocyclic or heterocyclic ring, which may comprise one or more heteroatoms selected in the group consisting of O, N and S; or R⁷ and R⁸, which may be the same or different, represent H, $C_1$-$C_6$ alkyl which may the same or different; or R⁷ and R⁸ may form a heterocyclic ring comprising further heteroatoms selected in the group consisting of O, S and N; or R⁹ represents H, methyl or ethyl; or R¹⁰ represents H, $C_1$-$C_4$-alkyl, $C_1$-$C_4$-alkoxy or NR⁷R⁸; or R¹¹ represents H; $C_1$-$C_4$-alkyl; $C_1$-$C_4$-halogenoalkyl; $C_1$-$C_4$-alkyl-phenyl wherein phenyl may substituted by F, Cl, Br, I, $C_1$-$C_4$-alkyl, $C_1$-$C_4$-halogenoalkyl or $C_1$-$C_4$-halogenoalkoxy; $C_1$-$C_4$-alkoxy-$C_1$-$C_4$-alkyl; phenoxy; benzyloxy; or R⁹ and R¹¹ may form a 5- or 6-membered heterocyclic ring comprising a further heteroatom selected in the group consisting of O, S and N; or m represents 1, 2, 3 or 4.

3. A compound of formula (I) according to claim 1 wherein
R¹ represents $C_1$-$C_{12}$-alkyl; or
R³ represents a non substituted $C_2$-$C_4$-alkyl, $C_3$-$C_4$-alkenyl or cyclopropyl; or
R² and R³ can form together a 6-membered heterocycle; or
R⁴ represents a non substituted $C_1$-$C_{12}$-alkyl, a fluorine or a chlorine atom; or
R⁵ represents a non substituted $C_1$-$C_{12}$-alkyl, a fluorine or a chlorine atom; or
m represents 1, 2 or 3.

4. A compound of formula (I) according to claim 1 wherein
R¹ represents methyl; or
R³ represents ethyl, n-propyl, i-propyl propenyl or allyl; or
R² and R³ can form together a pipiridinyl or a pyrrolidinyl; or
R⁴ represents methyl or ethyl; or
R⁵ represents methyl or ethyl.

5. A compound of formula (I) according to claim 1 wherein R² and R³ form together a 2-alkylated-pyrrolidinyl.

6. A compound of formula (I) according to claim 5 wherein R² and R³ form together a 2-methyl-pyrrolidinyl.

7. A process for the preparation of a compound of formula (I) according to claim 1 comprising the following steps:

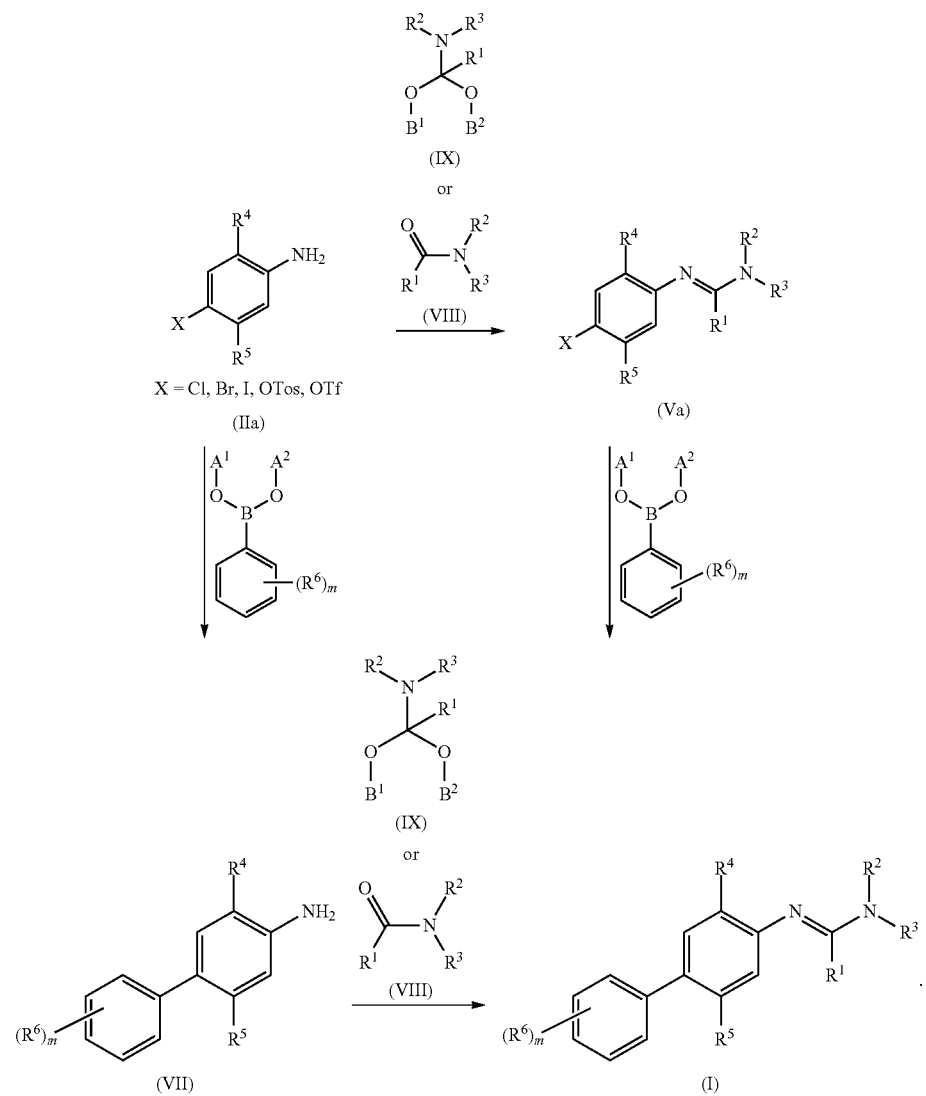

8. A method for controlling phytopathogenic fungi of crops, comprising applying an agronomically effective and substantially non-phytotoxic quantity of a compound according to claim 1 to soil where a plant grows or is capable of growing, and/or to the leaves and/or to fruit of a plant and/or to seed of a plant.

9. A method for controlling damaging insects comprising applying a compound of formula (I) according to claim 1 to seed, a plant and/or to fruit of a plant or to soil wherein the plant is growing or wherein said plant is desired to grow.

10. A compound of formula (I) according to claim 1 wherein $R^1$ represents H;

$R^2$ represents methyl;

$R^3$ represents $C_2$-$C_4$ alkyl;

$R^4$ represents methyl, ethyl, or a halogen atom;

$R^5$ H, methyl, or ethyl;

$R^6$ represents a halogen atom, $C_1$-$C_6$ halogenoalkyl, $C_1$-$C_6$ alkyl, phenoxy, $CR^9$=N—O—$R^{11}$;

$R^9$ represents H, methyl, or ethyl;

$R^{11}$ represents H or $C_1$-$C_4$ alkyl; and m represents 1.

11. A compound of formula (I) according to claim 1 wherein $R^1$ represents H;

$R^2$ represents methyl;

$R^3$ represents ethyl;

$R^4$ represents methyl or a chlorine atom;

$R^5$ represents H or methyl;

$R^6$ represents t-butyl, C=N—O-Me, O-Ph, CF3, or a chlorine atom; and m represents 1.

12. A compound of formula (I) according to claim 1 wherein $R^1$ represents H;

$R^2$ and $R^5$ represent methyl;

$R^3$ represents ethyl;

$R^4$ represents methyl or a chlorine atom;

$R^6$ represents t-butyl, C=N—O-Me, or O-Ph; and m represents 1.

13. A compound of formula (I) according to claim 1 wherein $R^1$ represents H;

$R^2$ and $R^4$ represent methyl;

$R^3$ represents ethyl;

$R^5$ represents H or methyl;

$R^6$ represents t-butyl, $CF_3$, or a chlorine atom; and m represents 1.

* * * * *